US012103973B2

(12) United States Patent
Huang et al.

(10) Patent No.: US 12,103,973 B2
(45) Date of Patent: Oct. 1, 2024

(54) ANTI-B7-H3 MONOCLONAL ANTIBODY AND USE THEREOF IN CELL THERAPY

(71) Applicants: FUZHOU TCELLTECH BIOTECHNOLOGY CO., LTD., Fuzhou (CN); Tcelltech Inc., Dover, DE (US)

(72) Inventors: Gangxiong Huang, Fuzhou (CN); Liqun Luo, Fuzhou (CN)

(73) Assignees: Fuzhou Tcelltech Biotechnology Co., Ltd., Fuzhou (CN); Tcelltech Inc., Dover, DE (US)

( * ) Notice: Subject to any disclaimer, the term of this patent is extended or adjusted under 35 U.S.C. 154(b) by 762 days.

(21) Appl. No.: 17/279,391

(22) PCT Filed: Sep. 26, 2019

(86) PCT No.: PCT/CN2019/108297
§ 371 (c)(1),
(2) Date: Mar. 24, 2021

(87) PCT Pub. No.: WO2020/063787
PCT Pub. Date: Apr. 2, 2020

(65) Prior Publication Data
US 2021/0395369 A1 Dec. 23, 2021

(30) Foreign Application Priority Data
Sep. 26, 2018 (CN) .......................... 201811125056.4

(51) Int. Cl.
| | |
|---|---|
| *C07K 16/28* | (2006.01) |
| *A61K 35/17* | (2015.01) |
| *A61K 38/00* | (2006.01) |
| *A61K 39/00* | (2006.01) |
| *A61K 47/68* | (2017.01) |
| *A61P 35/00* | (2006.01) |
| *C07K 14/705* | (2006.01) |
| *C07K 14/725* | (2006.01) |
| *C12N 5/0783* | (2010.01) |
| *G01N 33/68* | (2006.01) |

(52) U.S. Cl.
CPC .......... *C07K 16/2827* (2013.01); *A61K 35/17* (2013.01); *A61K 47/6849* (2017.08); *A61P 35/00* (2018.01); *C07K 14/7051* (2013.01); *C07K 14/70517* (2013.01); *C07K 14/70521* (2013.01); *C07K 14/70578* (2013.01); *C12N 5/0636* (2013.01); *G01N 33/68* (2013.01); *A61K 38/00* (2013.01); *A61K 2039/505* (2013.01); *C07K 2317/24* (2013.01); *C07K 2317/565* (2013.01); *C07K 2317/622* (2013.01); *C07K 2317/92* (2013.01); *C07K 2319/30* (2013.01); *C07K 2319/33* (2013.01); *C12N 2510/00* (2013.01); *G01N 2333/70532* (2013.01)

(58) Field of Classification Search
CPC ............ C07K 16/2827; C07K 14/7051; C07K 14/70517; C07K 14/70521; C07K 14/70578; C07K 2317/24; C07K 2317/565; C07K 2317/622; C07K 2317/92; C07K 2319/30; C07K 2319/33; C07K 2319/03; C07K 2319/24; C07K 2319/73; C07K 2319/92; C07K 14/7155; C07K 2319/00; C07K 2319/02; C07K 2319/21; C07K 2317/56; A61K 35/17; A61K 47/6849; A61K 38/00; A61K 2039/505; A61K 39/4611; A61K 2239/28; A61K 2239/31; A61K 2239/38; A61K 2239/50; A61K 2239/55; A61K 39/4631; A61K 39/464411; A61K 39/464429; A61K 2239/59; A61K 38/1774; A61K 38/1793; A61K 47/6801; A61K 47/6803; A61P 35/00; A61P 35/02; A61P 35/04; C12N 5/0636; C12N 2510/00; C12N 5/0645; C12N 5/0646; G01N 33/68; G01N 2333/70532; G01N 33/57484; G01N 33/57492; G01N 33/6893
See application file for complete search history.

(56) References Cited

U.S. PATENT DOCUMENTS 10,995,149 B2 * 5/2021 Chen .................. C07K 16/40
2020/0338209 A1 * 10/2020 Benatuil ................ A61P 35/00

FOREIGN PATENT DOCUMENTS

| AU | 2012/248470 A1 | 11/2013 |
|---|---|---|
| CN | 103687945 A | 3/2014 |

OTHER PUBLICATIONS

Herold et al., "Determinants of the assembly and function of antibody variable domains" (2017). Nature: Scientific Reports 7: 12276, pp. 1-17. (Year: 2017).*
Almagro et al., "Progress and challenges in the design and clinical development of antibodies for cancer therapy" (2018) Front. Immunol. vol. 8:1-19. (Year: 2018).*
International Search Report in PCT Appln. PCT/CN2019/108297 mailed Dec. 31, 2019; 3 pages.

* cited by examiner

*Primary Examiner* — Hong Sang
*Assistant Examiner* — Carol Ann Chase
(74) *Attorney, Agent, or Firm* — Kilpatrick Townsend & Stockton LLP

(57) ABSTRACT

The present invention provides an anti-B7-H3 monoclonal antibody and use thereof in cell therapy. Specifically, the present invention provides an scFv, an antibody, and a specific CAR-T cell specifically targeting B7-H3. The present invention further provides an engineered immune cell capable of co-expressing a CAR targeting B7-H3 and a chimeric molecule or a secreted protein of PD-L1, the engineered immune cell having good tumor killing effects.

15 Claims, 11 Drawing Sheets
Specification includes a Sequence Listing.

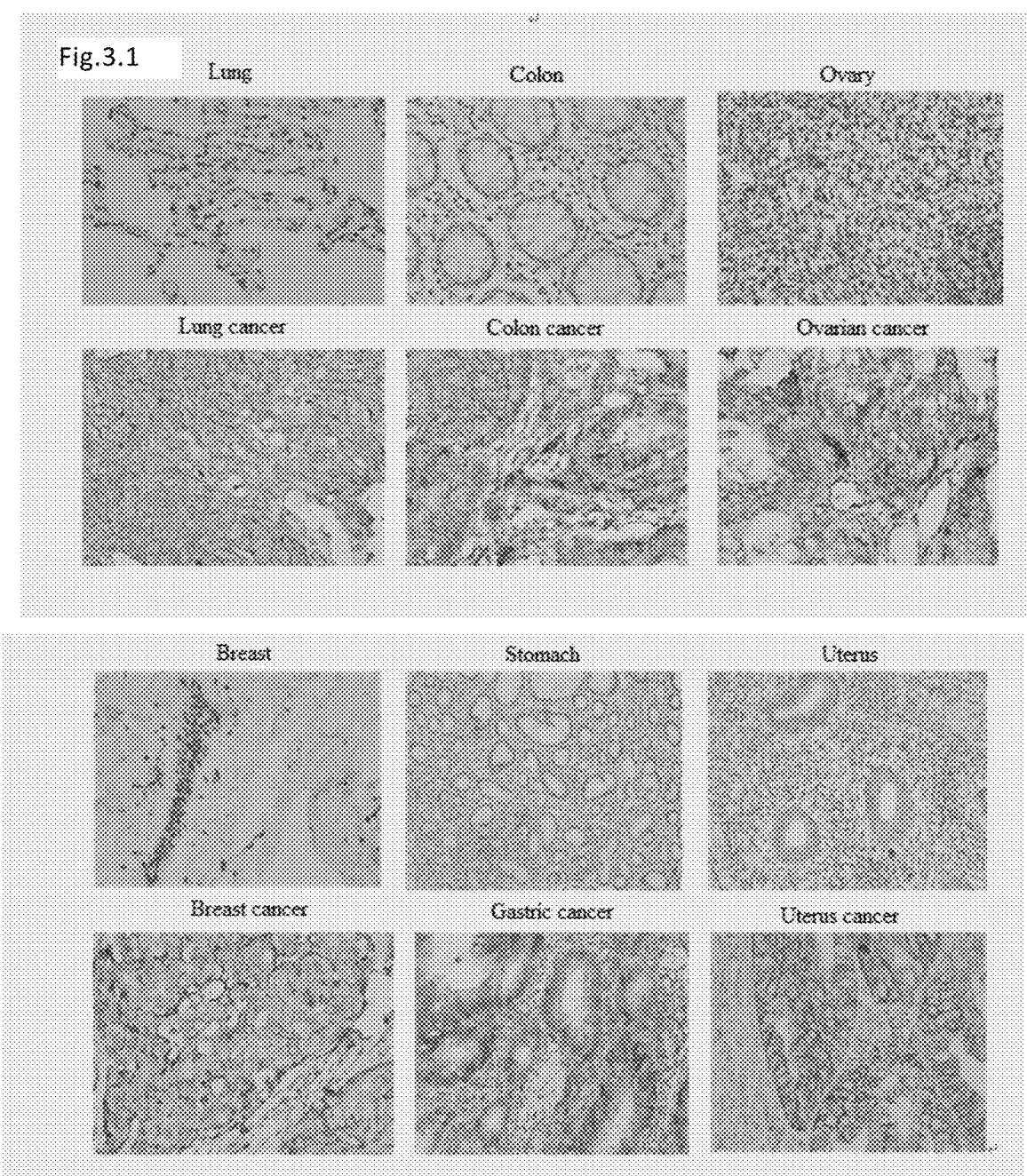
Fig.3.1

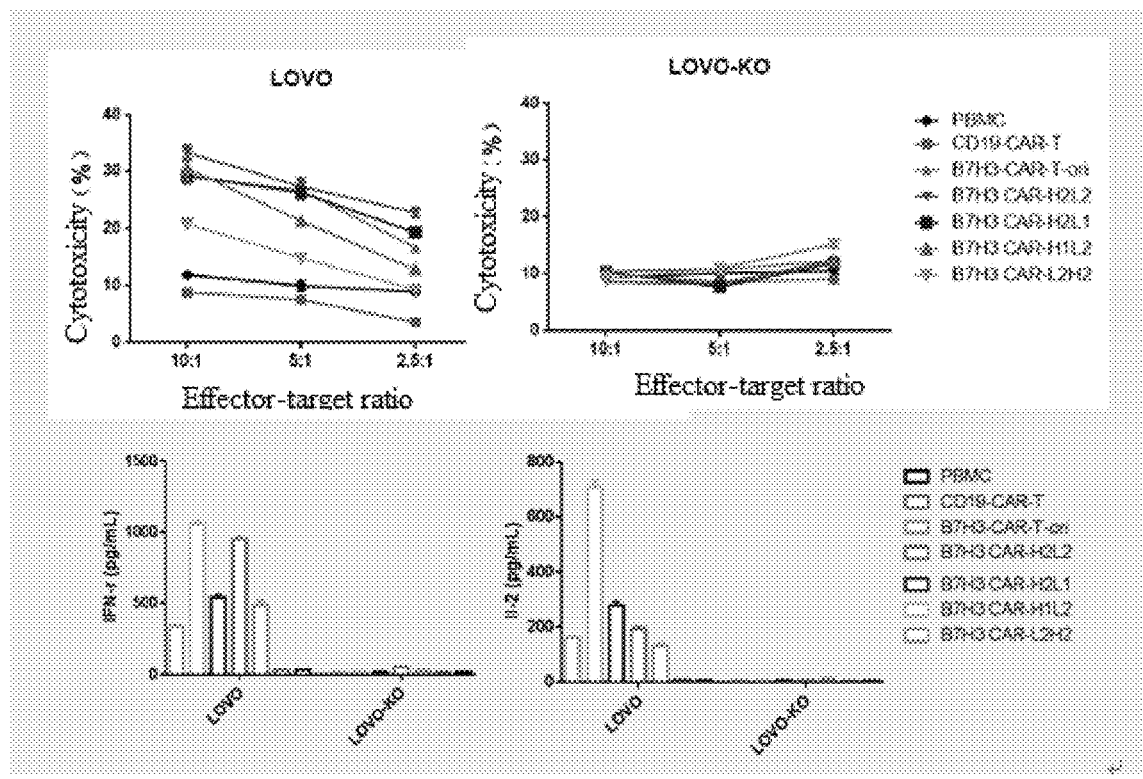
Fig. 10
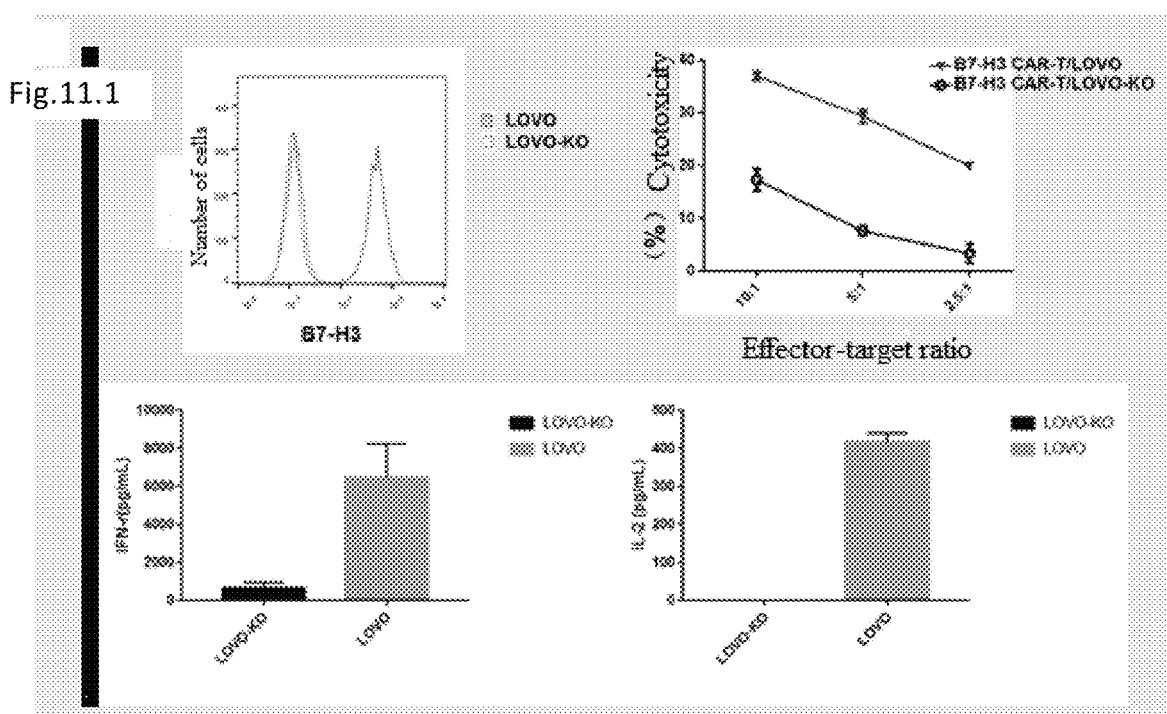
Fig. 11.1

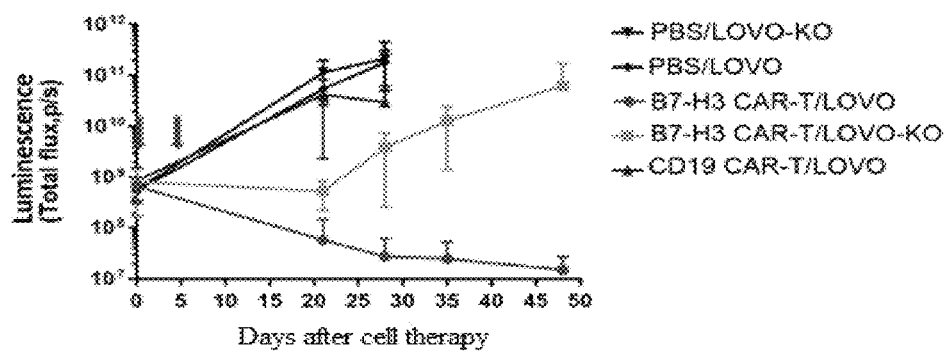
Fig. 11
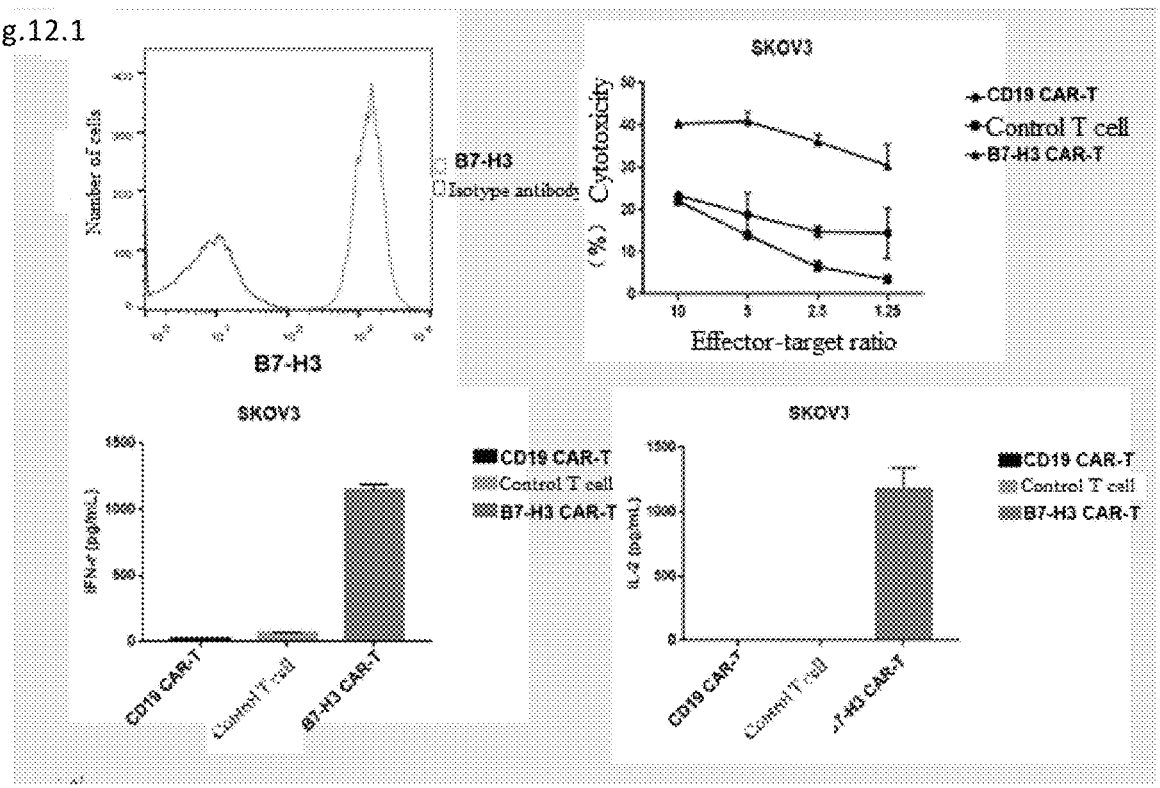

ANTI-B7-H3 MONOCLONAL ANTIBODY AND USE THEREOF IN CELL THERAPY

CROSS-REFERENCE TO RELATED APPLICATIONS

This application is a national phase application under 35 U.S.C. 371 claiming priority to PCT/CN2019/108297, filed Sep. 26, 2019, which application claims priority to CN 201811125056.4, filed Sep. 26, 2018, the disclosures of which are hereby incorporated by reference in their entirety for all purposes.

REFERENCE TO A "SEQUENCE LISTING," A TABLE, OR A COMPUTER PROGRAM LISTING APPENDIX SUBMITTED AS AN ASCII TEXT FILE

The Sequence Listing written in file P2020-2473_sequence_listing.txt, created on Mar. 23, 2021, 38,799 bytes, machine format IBM-PC, MS-Windows operating system, is hereby incorporated by reference in its entirety for all purposes.

FIELD OF THE INVENTION

The present invention relates to the field of biomedicine, and specifically to anti-B7-H3 monoclonal antibody and application thereof in cell therapy.

BACKGROUND OF THE INVENTION

Targeting molecules expressed by tumor cells are the main determinant for tumors to be recognized and used for treatment. At present, various tumor treating technologies, including targeted therapy and immunotherapy means such as antibodies or/and CAR-T cells, all rely on specific targeting molecules expressed in tumors and the related components thereof. The specificity of targeting molecules is closely related to the efficacy of tumor treatment, degree of side effects of treatments and the like. B7-H3 (CD276) is not expressed or very lowly expressed in normal tissues and cells, but highly expressed in most solid malignant tumor cells and vascular endothelial cells in tumors or other cellular components of tumor microenvironments, and is a good specific tumor targeting molecule.

A monoclonal antibody is an antibody produced by a single B cell clone against a specific epitope. Monoclonal antibodies have been widely used in biological and medical research, clinical diagnosis and treatment, etc. by recognizing specific targeting molecules.

Chimeric antigen receptor T cell therapy is a technology method for performing genetic modification of chimeric antigen receptors (CARs) on T cells to form CAR-expressing T cells (CAR-T), and then feeding back the CAR-T cells to the body for treatment. The CAR-T cell therapy for tumors is a hot field of current research and application development. Generally, CAR-T cells recognize specific targeting molecules on tumor cells through single-chain antibody variable regions (scFv) on CAR molecules and kill the tumor cells, thereby exerting an anti-tumor immune effect.

At present, the efficacy of antibodies against B7-H3 targeting molecules in the treatment of tumors is not clear. This antibody is mainly used for clinical application as a block and regulation of the inhibitory molecules on immune cells. However, because the immune function mechanism of the B7-H3 molecule is not yet clear, the efficacy thereof is not yet known.

At present, the efficacy of CAR-T cells in the treatment of solid tumors is still not good. Effective tumor-specific targeting molecules are one of the main factors in CAR-T cell therapy. The CAR-T cell therapy against the currently known targeting molecules of solid tumors has not yet achieved exact and lasting efficacy.

Therefore, there is an urgent need in the art to develop a class of antibodies that specifically target B7-H3 and have good tumor killing effects, and corresponding engineered immune cells.

SUMMARY OF THE INVENTION

The objective of the present invention is to provide a class of antibodies that specifically target B7-H3 and have good tumor killing effects, and corresponding engineered immune cells.

The first aspect of the present invention provides a heavy chain variable region of an antibody, the heavy chain variable region including the following three complementary determining regions (CDRs):
CDR1 as shown in SEQ ID NOs: 1, 2 or 3,
CDR2 as shown in SEQ ID NOs: 4, 5 or 6, and
CDR3 as shown in SEQ ID NOs: 7, 8 or 9.

In another preferred example, the CDRs of the heavy chain variable region include 3 CDRs as shown in SEQ ID NOs: $N_H$, $N_H+3$, and $N_H+6$, wherein $N_H$ is 1, 2 or 3, respectively.

In another preferred example, any one of the abovementioned amino acid sequences further includes a derived sequence in which at least one amino acid (for example, 1-3, preferably 1-2, more preferably 1) is optionally added, deleted, modified and/or substituted and that can retain the binding affinity of B7-H3.

In another preferred example, the heavy chain variable region further includes a humanized FR region or a murine FR region.

In another preferred example, the heavy chain variable region has an amino acid sequence as shown in any one of SEQ ID NOs: 19-24.

The second aspect of the present invention provides a heavy chain of an antibody, the heavy chain having the heavy chain variable region according to the first aspect of the present invention.

In another preferred example, the heavy chain of the antibody further includes a heavy chain constant region.

In another preferred example, the heavy chain constant region is of humanized, murine or rabbit origin.

The third aspect of the present invention provides a light chain variable region of an antibody, the light chain variable region including the following three complementary determining regions (CDRs):
CDR1' as shown in SEQ ID NO: 10, 11 or 12,
CDR2' as shown in SEQ ID NO: 13, 14 or 15, and
CDR3' as shown in SEQ ID NO: 16, 17, or 18.

In another preferred example, the CDRs of the light chain variable region include 3 CDRs as shown in SEQ ID NO: $N_L$, $N_L+3$, and $N_L+6$, wherein $N_L$ is 10, 11 or 12, respectively.

In another preferred example, any one of the abovementioned amino acid sequences further includes a derived sequence in which at least one amino acid (for example, 1-3, preferably 1-2, more preferably 1) is optionally added, deleted, modified and/or substituted and that can retain the binding affinity of B7-H3.

In another preferred example, the light chain variable region further includes a human FR region or a murine FR region.

In another preferred example, the light chain variable region has an amino acid sequence as shown in any one of SEQ ID NOs: 25-30.

The fourth aspect of the present invention provides a light chain of an antibody, the light chain having the light chain variable region according to the third aspect of the present invention.

In another preferred example, the light chain of the antibody further includes a light chain constant region.

In another preferred example, the light chain constant region is of human, murine or rabbit origin.

The fifth aspect of the present invention provides an antibody, the antibody having:

(1) the heavy chain variable region according to the first aspect of the present invention; and/or (2) the light chain variable region according to the third aspect of the present invention.

In another preferred example, the antibody has: the heavy chain according to the second aspect of the present invention; and/or the light chain according to the fourth aspect of the present invention.

In another preferred example, the affinity Ka(1/Ms) of the antibody to human B7-H3 (wild type) is $\geq 2\times 10^4$ (for example, $3\times 10^4 \sim 1.5\times 10^5$), preferably $\geq 4\times 10^4$, more preferably $\geq 5\times 10^4$.

In another preferred example, the affinity Kd(1/s) of the antibody to human B7-H3 (wild type) is $\leq 5\times 10^{-4}$ (for example, $5\times 10^{-6} \text{-} 5\times 10^{-4}$), preferably $\leq 4\times 10^{-4}$, more preferably $\leq 3\times 10^{-4}$.

In another preferred example, the affinity KD(M) of the antibody to human B7-H3 (wild type) is $\leq 8\times 10^{-9}$ (for example, $1.0\times 10^{-10} 8\times 10^{-9}$), preferably $\leq 6\times 10^{-9}$, more preferably $\leq 5\times 10^{-9}$.

In another preferred example, the antibody has affinity Ka(1/Ms) of 8.89E+4, Kd(1/s) of 8.72E-6, and KD(M) of 9.81E-11 to human B7-H3 (preferably wild type).

In another preferred example, the antibody has affinity Ka(1/Ms) of 6.13E+4, Kd(1/s) of 2.30E-4, and KD(M) of 3.76E-9 to human B7-H3 (preferably wild type). (Humanized HC1+LC1)

In another preferred example, the antibody has affinity Ka(1/Ms) of 4.12E+4, Kd(1/s) of 6.44E-5, and KD(M) of 1.56E-9 to human B7-H3 (preferably wild type). (Humanized HC1+LC2)

In another preferred example, the antibody has affinity Ka(1/Ms) of 4.11E+4, Kd(1/s) of 1.78E-4, and KD(M) of 4.34E-9 to human B7-H3 (preferably wild type). (Humanized HC1+LC3)

In another preferred example, the antibody has affinity Ka(1/Ms) of 5.29E+4, Kd(1/s) of 3.06E-5, and KD(M) of 5.78E-10 to human B7-H3 (preferably wild type). (Humanized HC2+LC1)

In another preferred example, the antibody has affinity Ka(1/Ms) of 5.48E+4, Kd(1/s) of 2.34E-5, and KD(M) of 4.28E-10 to human B7-H3 (preferably wild type). (Humanized HC2+LC2)

In another preferred example, the antibody has affinity Ka(1/Ms) of 6.73E+4, Kd(1/s) of 8.74E-6, and KD(M) of 1.30E-10 to human B7-H3 (preferably wild type). (Humanized HC2+LC3)

In another preferred example, the antibody has affinity Ka(1/Ms) of 7.16E+4, Kd(1/s) of 3.33E-5, and KD(M) of 4.66E-10 to human B7-H3 (preferably wild type). (Humanized HC3+LC1)

In another preferred example, the antibody has affinity Ka(1/Ms) of 6.24E+4, Kd(1/s) of 3.26E-5, and KD(M) of 5.23E-10 to human B7-H3 (preferably wild type). (Humanized HC3+LC2)

In another preferred example, the antibody has affinity Ka(1/Ms) of 4.25E+4, Kd(1/s) of 1.96E-5, and KD(M) of 4.62E-10 to human B7-H3 (preferably wild type). (Humanized HC3+LC3)

In another preferred example, the antibody is selected from the group consisting of animal-derived antibodies, chimeric antibodies, humanized antibodies, and combinations thereof.

In another preferred example, the antibody is a double-chain antibody or a single-chain antibody.

In another preferred example, the antibody is a monoclonal antibody.

In another preferred example, the antibody is a partially or fully humanized monoclonal antibody.

In another preferred example, the sequence of the heavy chain variable region of the antibody is shown in any one of SEQ ID NOs: 19-24; and/or
the sequence of the light chain variable region of the antibody is shown in any one of SEQ ID NOs: 25-30.

In another preferred example, the antibody is of an IgG type.

In another preferred example, the antibody is in the form of a drug conjugate.

The sixth aspect of the present invention provides a recombinant protein, the recombinant protein having:

(i) the heavy chain variable region according to the first aspect of the present invention, the heavy chain according to the second aspect of the present invention, the light chain variable region according to the third aspect of the present invention, the light chain according to the fourth aspect of the present invention, or the antibody according to the fifth aspect of the present invention; and (ii) an optional tag sequence assisting expression and/or purification.

In another preferred example, the tag sequence includes a 6His tag.

In another preferred example, the recombinant protein (or polypeptide) includes a fusion protein.

In another preferred example, the recombinant protein is a monomer, dimer, or multimer.

The seventh aspect of the present invention provides a CAR construct, the antigen binding region of the CAR construct is scFv that specifically binds to B7-H3, and the scFv has the heavy chain variable region according to the first aspect of the present invention and the light chain variable region according to the third aspect of the present invention.

In another preferred example, the structure of the CAR is shown in the following formula I:

$$\text{L-scFv-H-TM-C-CD3}\zeta\text{-Z-P} \qquad (I)$$

in the formula,
each "-" is independently a linker peptide or a peptide bond;
L is none or a signal peptide sequence;
scFv is a single-chain variable region sequence targeting B7-H3;
H is none or a hinge region;
TM is a transmembrane domain;

C is a costimulatory signal molecule;

CD3ζ is a cytoplasmic signal transduction sequence derived from CD3ζ;

Z is none or a coding sequence of self-cleaving protein;

P is none or a coding sequence of a fusion protein containing PD1-CD28 or PD1-IL7R.

In another preferred example, the structure of the scFv is as shown in formula A1 or A2:

$$V_L\text{-}V_H \quad (A1); \text{ or}$$

$$V_H\text{-}V_L \quad (A2)$$

wherein, $V_L$ is the light chain variable region of the anti-B7-H3 antibody; $V_H$ is the heavy chain variable region of the anti-B7-H3 antibody; and "-" is a linker peptide (or flexible linker) or peptide bond.

In another preferred example, the structures of formulas A1 and A2 are from the N-terminal to the C-terminal.

In another preferred example, the $V_L$ and $V_H$ are connected by a flexible linker.

In another preferred example, the flexible linker is a sequence shown by 1-5 (preferably 2-4, more preferably 3-4) consecutive $(G)_4S$.

In another preferred example, the $V_L$ and $V_H$ are each independently of murine, humanized, rabbit, or human origin.

In another preferred example, the amino acid sequence of $V_L$ includes $V_L$ selected from any one of SEQ ID Nos.: 25-30 or derivative $V_L$ thereof (or an active fragment thereof).

In another preferred example, the amino acid sequence of $V_H$ includes $V_H$ selected from any one of SEQ ID Nos.: 19-24 or derivative $V_H$ (or an active fragment thereof).

In another preferred example, the scFv is a murine, humanized, humanized and murine chimeric, or fully humanized single-chain antibody variable region fragment.

In another preferred example, L is a signal peptide of a protein selected from the group consisting of CD8, CD28, GM-CSF, CSF2RB, CD4, CD137, IL-2, IFNr, and a combination thereof.

In another preferred example, H is a hinge region of a protein selected from the group consisting of CD8, CD28, CD137, CD80, CD86, and a combination thereof.

In another preferred example, TM is a transmembrane region of a protein selected from the group consisting of CD28, CD3 epsilon, CD45, CD4, CD5, CD8, CD9, CD16, CD22, CD33, CD37, CD64, CD80, CD86, CD134, CD137, CD154, and a combination thereof.

In another preferred example, C is a costimulatory signal molecule of a protein selected from the group consisting of OX40, CD2, CD7, CD27, CD28, CD30, CD40, CD70, CD134, 4-1BB (CD137), PD1, Dap10, CDS, ICAM-1, LFA-1 (CD11a/CD18), ICOS (CD278), NKG2D, GITR, TLR2, and a combination thereof.

In another preferred example, C is a costimulatory signal molecule derived from CD28 and/or 4-1BB (CD137).

In another preferred example, the self-cleaving protein is selected from the group consisting of T2A, P2A, E2A, F2A, and a combination thereof.

In another preferred example, the self-cleaving protein is selected from the group consisting of furin-V5-SGSG-T2A, furin-V5-SGSG-P2A, furin-V5-SGSG-E2A, furin-V5-SGSG-F2A, and a combination thereof.

In another preferred example, the self-cleaving protein is selected from the group consisting of furin-SGSG-T2A, furin-SGSG-P2A, furin-SGSG-E2A, furin-SGSG-F2A, and a combination thereof.

In another preferred example, the structure of the fusion protein is shown in formula II:

$$L1\text{-}I1\text{-}L2\text{-}H1\text{-}TM1\text{-}C1 \quad (II)$$

in the formula, each "-" is independently a linker peptide or peptide bond;

L1 is none or a signal peptide sequence;

I1 is an extracellular fragment of PD-1;

L2 is none or a linker peptide component;

H1 is an optional hinge region;

TM1 is none or a transmembrane domain;

C1 is none or an intracellular domain.

In another preferred example, L1 is a signal peptide of a protein selected from the group consisting of GM-CSF, CD4, CD8, IL-2, IFNr, TNF, and a combination thereof.

In another preferred example, the signal peptide sequence of L1 is MALPVTALLLPLALLLHAARP (SEQ ID NO: 31).

In another preferred example, the extracellular fragment of PD-1 has an amino acid sequence as shown in SEQ ID NO: 32.

In another preferred example, the amino acid sequence of the extracellular fragment of PD-1 is as shown in SEQ ID NO: 32.

In another preferred example, the linker peptide component is a sequence of 1-9 (preferably 2-7, more preferably 2-4) consecutive $G_4S$, mlgG3UH, LFL, cTPRs, ZAG, β2m, polyPro (Glyc), polyPro, GlySer(Glyc), and a combination thereof.

In another preferred example, H1 is a hinge region of a protein selected from the group consisting of IgG4, CD8, CD28, CD137, and a combination thereof.

In another preferred example, TM1 is a transmembrane region of a protein selected from the group consisting of CD4, CD8, CD28, and a combination thereof.

In another preferred example, TM1 is a transmembrane region of a protein selected from the group consisting of CD28.

In another preferred example, TM1 has an amino acid sequence as shown in SEQ ID NO: 33.

In another preferred example, the amino acid sequence of TM1 is as shown in SEQ ID NO: 33.

In another preferred example, C1 is an intracellular fragment of a protein selected from the group consisting of CD137, CD28, IL-7R, and a combination thereof.

In another preferred example, C1 is an intracellular fragment derived from CD28 and/or IL-7R.

In another preferred example, C1 has an amino acid sequence as shown in SEQ ID NO: 34.

In another preferred example, P component has an amino acid sequence as shown in SEQ ID NO: 35.

In another preferred example, the coding sequence of the P component has a nucleotide sequence as shown in SEQ ID NO: 36.

In another preferred example, the amino acid sequence of CAR is as shown in SEQ ID NO: 37.

In another preferred example, the coding sequence of CAR is shown in SEQ ID NO: 38.

The eighth aspect of the present invention provides an engineered immune cell, the immune cell including:

(a) a first expression cassette for expressing the exogenous CAR construct according to the seventh aspect of the present invention; and (b) an optional second expression cassette for expressing a fusion protein containing PD1-CD28 or PD1-IL7R.

In another preferred example, the first expression cassette and the second expression cassette are connected (or connected in series) by the coding sequence of a self-cleaving protein.

In another preferred example, the self-cleaving protein is selected from the group consisting of T2A, P2A, E2A, F2A, and a combination thereof.

In another preferred example, the self-cleaving protein is selected from the group consisting of furin-V5-SGSG-T2A, furin-V5-SGSG-P2A, furin-V5-SGSG-E2A, furin-V5-SGSG-F2A, and a combination thereof.

In another preferred example, the self-cleaving protein is selected from the group consisting of furin-SGSG-T2A, furin-SGSG-P2A, furin-SGSG-E2A, furin-SGSG-F2A, and a combination thereof.

In another preferred example, the structure of the fusion protein is as shown in formula II:

L1-I1-L2-H1-TM1-C1       (II)

in the formula,
each "-" is independently a linker peptide or peptide bond;
L1 is none or a signal peptide sequence;
I1 is an extracellular fragment of PD-1;
L2 is none or a linker peptide component;
H1 is an optional hinge region;
TM1 is none or a transmembrane domain;
C1 is none or an intracellular domain.

In another preferred example, the fusion protein has an amino acid sequence as shown in SEQ ID NO: 35.

In another preferred example, the coding sequence of the fusion protein has a nucleotide sequence as shown in SEQ ID NO: 36.

In another preferred example, the first expression cassette contains a nucleotide sequence encoding the CAR construct of claim 7.

In another preferred example, the second expression cassette contains a nucleotide sequence encoding the fusion protein.

In another preferred example, the first expression cassette and the second expression cassette further include a promoter and/or a terminator, respectively.

In another preferred example, the promoter is a mammalian promoter, preferably hEF1.

In another preferred example, the sequence of the promoter is as shown in SEQ ID NO: 39.

In another preferred example, the first expression cassette and the second expression cassette are on a vector or integrated into a chromosome of the engineered immune cell.

In another preferred example, the first expression cassette and the second expression cassette are independent or connected.

In another preferred example, the first expression cassette and the second expression cassette are in the same or different vectors.

In another preferred example, the first expression cassette and the second expression cassette are in the same vector.

In another preferred example, the vector is selected from the group consisting of DNA, RNA, plasmid, lentiviral vector, adenoviral vector, retroviral vector, transposon, oncolytic viral vector, other gene transfer system, and a combination thereof.

In another preferred example, the vector is a lentiviral vector.

In another preferred example, the vector is a transposon vector.

In another preferred example, the cell is a mammalian cell.

In another preferred example, the immune cell is ex vivo.

In another preferred example, the immune cell is autologous.

In another preferred example, the immune cell is non-autologous.

In another preferred example, the immune cell is derived from human or non-human mammal (for example, murine).

In another preferred example, the immune cell is derived from a primate (preferably human).

In another preferred example, the immune cell is selected from the group consisting of:
(i) chimeric antigen receptor T cell (CAR-T cell);
(ii) chimeric antigen receptor NK cell (CAR-NK cell); or
(iii) exogenous T cell receptor (TCR) T cell (TCR-T cell)

In another preferred example, the immune cell includes: NK cell, T cell, NKT cell, (γδ) T cell, monocyte, or macrophage.

The ninth aspect of the present invention provides an antibody-drug conjugate, including:
(a) an antibody portion, selected from the group consisting of the heavy chain variable region according to the first aspect of the present invention, the heavy chain according to the second aspect of the present invention, the light chain variable region according to the third aspect of the present invention, the light chain according to the fourth aspect of the present invention, or the antibody according to the fifth aspect of the present invention, or combination thereof; and
(b) a conjugating portion conjugated to the antibody portion, the conjugating portion being selected from the group consisting of detectable markers, drugs, toxins, cytokines, radionuclides, enzymes, and combinations thereof.

In another preferred example, the antibody portion and the conjugating portion are conjugated through a chemical bond or linker.

The tenth aspect of the present invention provides the uses of the heavy chain variable region according to the first aspect of the present invention, the heavy chain according to the second aspect of the present invention, the light chain variable region according to the third aspect of the present invention, the light chain according to the fourth aspect of the present invention, the antibody according to the fifth aspect of the present invention, the recombinant protein according to the sixth aspect of the present invention, the CAR construct according to the seventh aspect of the present invention, the immune cell according to the eighth aspect of the present invention, or the antibody-drug conjugate according to the ninth aspect of the present invention, for (i) preparing a drug or preparation for preventing and/or treating a cancer or tumor; and/or (ii) preparing a detection reagent or kit.

In another preferred example, the tumor is selected from the group consisting of hematological tumor, solid tumor, and a combination thereof.

In another preferred example, the hematological tumor is selected from the group consisting of acute myeloid leukemia (AML), multiple myeloma (MM), chronic lymphocytic leukemia (CLL), acute lymphocytic leukemia (ALL), diffuse large B cell lymphoma (DLBCL), and a combination thereof.

In another preferred example, the solid tumor is selected from the group consisting of gastric cancer, gastric cancer peritoneal metastasis, liver cancer, leukemia, kidney tumor, lung cancer, small intestinal cancer, bone cancer, osteosarcoma, prostate cancer, colorectal cancer, breast cancer, colorectal cancer, cervical cancer, ovarian cancer, lymphoma, nasopharyngeal cancer, adrenal tumor, bladder tumor, non-small cell lung cancer (NSCLC), nervous system tumor, glioma, neuroblastoma, metastatic malignant tumor, abdominal metastasis of solid tumor, pelvic metastasis of solid tumor, and a combination thereof.

In another preferred example, the solid tumor is selected from the group consisting of head and neck tumors, throat cancer, lung cancer, non-small cell lung cancer, bronchial cancer, gastric cancer, peritoneal metastasis tumor of gastric cancer, esophageal cancer, liver cancer, bile duct cancer, pancreatic cancer, colorectal cancer, peritoneal metastatic tumor of colorectal cancer, small intestinal cancer, kidney tumor, kidney cancer, bladder tumor, transitional epithelial malignancies, endocrine tumors, thyroid cancer, adrenal tumors, breast cancer, cervical cancer, ovarian cancer, peritoneal metastatic tumor of ovarian cancer, endometrial cancer, choriocarcinoma, prostate cancer, testicular tumor, germ cell tumor, seminoma, embryogenic tumor, nervous system tumor, brain glioma, neuroblastoma, skin tumor, malignant melanoma, lymphoma, thymic tumor, nasopharyngeal cancer, bone cancer, sarcoma, rhabdomyosarcoma, liposarcoma, angiosarcoma, leiomyosarcoma, fibrosarcoma, osteosarcoma, Ewing's sarcoma, solid metastatic tumors at the abdominal cavity, thoracic cavity, pelvic cavity and parenchymatous organs, and a combination thereof.

In another preferred example, the tumor expresses or highly expresses B7-H3.

In another preferred example, the tumor includes a B7-H3-positive tumor.

In another preferred example, the tumor includes tumors that are positive for tumor vascular endothelial cells.

In another preferred example, the tumor includes a B7-H3-positive tumor in a tumor microenvironment.

In another preferred example, the antibody includes the antibody in the form of drug conjugate (ADC).

In another preferred example, the detection reagent or kit is used to diagnose a tumor that expresses or highly expresses B7-H3.

In another preferred example, the detection reagent or kit is used to detect B7-H3 protein in a sample.

In another preferred example, the detection reagent is a test chip.

The eleventh aspect of the present invention provides a pharmaceutical composition, including:

the heavy chain variable region according to the first aspect of the present invention, the heavy chain according to the second aspect of the present invention, the light chain variable region according to the third aspect of the present invention, the light chain according to the fourth aspect of the present invention, or the antibody according to the fifth aspect of the present invention, the recombinant protein according to the sixth aspect of the present invention, the CAR construct according to the seventh aspect of the present invention, the immune cell according to the eighth aspect of the present invention, and/or the antibody-drug conjugate according to the ninth aspect of the present invention, and a pharmaceutically acceptable carrier, diluent or excipient.

In another preferred example, the pharmaceutical composition is liquid preparation.

In another preferred example, the dosage form of the pharmaceutical composition is injection.

In another preferred example, in the pharmaceutical composition, the concentration of cells is $1\times10^3$-$1\times10^9$ cells/ml, preferably $1\times10^5$-$1\times10^8$ cells/ml.

In another preferred example, the pharmaceutical composition further contains other drugs (such as nucleic acid drugs, antibody drugs, targeted drugs, other immune cell drugs, other CAR-T drugs, chemotherapy drugs, or combinations thereof) that selectively kill tumor cells.

In another preferred example, the antibody drug includes a PD-1 inhibitor or a PD-L1 inhibitor.

In another preferred example, the inhibitor is selected from the group consisting of antibodies, small molecule compounds, microRNA, siRNA, shRNA, and combinations thereof.

The twelfth aspect of the present invention provides a polynucleotide, the polynucleotide encoding polypeptides selected from the group consisting of:

(1) the heavy chain variable region according to the first aspect of the present invention, the heavy chain according to the second aspect of the present invention, the light chain variable region according to the third aspect of the present invention, the light chain according to the fourth aspect of the present invention, or the antibody according to the fifth aspect of the present invention;

(2) the recombinant protein according to the sixth aspect of the present invention; and (3) the CAR construct according to the seventh aspect of the present invention.

The thirteenth aspect of the present invention provides a vector, comprising the polynucleotide according to the twelfth aspect of the present invention.

In another preferred example, the vector includes: bacterial plasmid, phage, yeast plasmid, plant cell virus, mammalian cell virus such as adenovirus, retrovirus, or other vectors.

The fourteenth aspect of the present invention provides a genetically engineered host cell, the host cell contains the vector according to the thirteenth aspect of the present invention or the polynucleotide according to the twelfth aspect of the present invention is integrated into the genome of the host cell.

The fifteenth aspect of the present invention provides a method for preparing an engineered immune cell, including the following steps:

(A) providing an immune cell to be modified; and (B) introducing the first expression cassette and/or the optional second expression cassette into the immune cell to be modified, wherein the first expression cassette expresses the CAR construct according to the seventh aspect of the present invention, and the second expression cassette expresses a fusion protein containing PD1-CD28 or PD1-IL7R, thereby obtaining the engineered immune cell.

In another preferred example, in step (B), including (B1) introducing the first expression cassette expressing the CAR construct according to the seventh aspect of the present invention into the immune cell; and optionally, (B2) introducing the second expression cassette expressing the fusion protein into the immune cell; wherein step (B1) may be performed before, after, simultaneously, or alternately with step (B2).

In another preferred example, the first expression cassette contains a nucleotide sequence encoding the CAR construct according to the seventh aspect of the present invention.

In another preferred example, the second expression cassette contains a nucleotide sequence encoding the fusion protein.

In another preferred example, the first expression cassette and the second expression cassette are in a vector or integrated into a chromosome of the engineered immune cell.

In another preferred example, the first expression cassette and the second expression cassette are in the same or different vectors.

In another preferred example, the first expression cassette and the second expression cassette are in the same vector.

In another preferred example, the vector is selected from the group consisting of DNA, RNA, plasmid, lentiviral vector, adenoviral vector, retroviral vector, transposon, oncolytic viral vector, other gene transfer systems, and a combination thereof.

In another preferred example, the vector is a viral vector (such as a lentiviral vector).

In another preferred example, the vector is a transposon vector.

In another preferred example, the immune cell is a T cell or NK cell.

In another preferred example, the method further includes the step of performing function and effectiveness test on the obtained engineered immune cell.

The sixteenth aspect of the present invention provides a method for testing B7-H3 protein in a sample in vitro, including the following steps:

(1) contacting the sample with the antibody according to the fifth aspect of the present invention in vitro; and (2) testing whether an antigen-antibody complex is formed, wherein the formation of the complex indicates the presence of the B7-H3 protein in the sample.

In another preferred example, the method is non-diagnostic and non-therapeutic.

The seventeenth aspect of the present invention provides a test plate, the test plate including: a substrate (support plate) and a test strip, the test strip containing the antibody according to the fifth aspect of the present invention or the antibody-drug conjugate according to the ninth aspect of the present invention.

The eighteenth aspect of the present invention provides a kit for preparing the engineered immune cell according to the eighth aspect of the present invention, wherein the kit includes:

(a) a first container, and a first nucleotide sequence in the first container, the first nucleotide sequence containing a first expression cassette for expressing the CAR construct of claim 7; and optionally (b) a second container, and a second nucleotide sequence in the second container, the second nucleotide sequence containing a second expression cassette for expressing the fusion protein.

In another preferred example, the first and second nucleotide sequences are independent or connected.

In another preferred example, the first and second nucleotide sequences are in the same or different containers.

In another preferred example, the first and second nucleotide sequences are in the same or different vectors.

In another preferred example, the first and second nucleotide sequences are in the same vector.

The nineteenth aspect of the present invention provides a diagnostic kit, including:

(1) a first container containing the antibody according to the fifth aspect of the present invention; and/or (2) a second container containing a secondary antibody against the antibody according to the fifth aspect of the present invention.

In another preferred example, the kit contains the test plate according to the seventeenth aspect of the present invention.

The twentieth aspect of the present invention provides a method for treating a cancer or tumor, including: administering the antibody according to the fifth aspect of the present invention, the recombinant protein according to the sixth aspect of the present invention, the CAR construct according to the seventh aspect of the present invention, the immune cell according to the eighth aspect of the present invention, the antibody-drug conjugate according to the ninth aspect of the present invention, or the pharmaceutical composition according to the eleventh aspect of the present invention, to a subject in need.

It should be understood that, within the scope of the present invention, the above-mentioned technical features of the present invention and the technical features specifically described in the following (such as the embodiments) can be combined with each other to form new or preferred technical solutions. Due to space limitations, details are not described herein again.

BRIEF DESCRIPTION OF THE DRAWINGS

FIG. 3-1: immunohistochemical staining of paraffin sections of multiple tumors, and microscopic observation of the staining results. FIG. 3-2: tumor cells were stained using a B7-H3 monoclonal antibody as a primary antibody and an APC-tagged anti-mIgG monoclonal antibody as a secondary antibody, and the expression of B7-H3 on various tumor cell membranes is tested by flow cytometry; mouse IgG1 is used as the control of the primary antibody of the same type.

Figure 5:
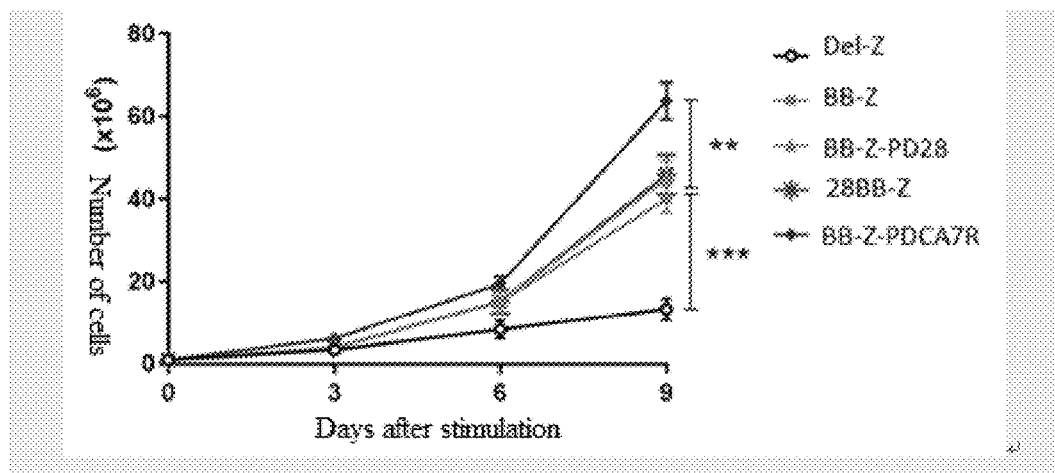

Respectively: ① B7-H3 CAR (B7-H3 Del-Z-CAR; Del-Z) containing anti-B7-H3 single-chain antibody and with 4-1BB truncated and CD3 deleted; ② B7-H3 CAR (B7-H34-1BB-CAR; BB-Z) containing anti-B7-H3 single-chain antibody, 4-1BB and CD3ζ intracellular functional fragments; ③ B7-H34-1BB-CAR (BB-Z-PD28) co-expressing a PD-1-CD28 chimeric molecule; the PD1-CD28 chimeric molecule refers to a chimeric molecule in which the extracellular fragment of a PD-1 molecule is connected to the intracellular segment of a CD28 molecule; ④ B7-H34-1BB-CAR (BB-Z-PDCA7R) co-expressing PD-1-IL-7R chimeric molecule; the PD1-IL-7R chimeric molecule refers to a chimeric molecule in which the extracellular fragment of a PD-1 molecule is connected to the intracellular segment of an interleukin 7 receptor (IL-7R) molecule or variant thereof; ⑤ B7-H3 CAR (B7-H3 CD28-4-1BB-CAR; 28BB-Z) containing anti-B7-H3 single-chain antibody and CD28, 4-1BB and CD3ζ intracellular functional fragments;

FIG. 5: cell proliferation response of B7-H3CAR-T cells of different structures to B7-H3 target cell antigen stimulation. B7-H3 CAR-T cell (BB-Z-PDCA7R) co-expressing the PD-1-IL-7R chimeric molecule has the best proliferation ability; B7-H34-1BB-CAR T cell (BB-Z), B7-H3 CD28-4-1BB-CAR T cell (28BB-Z), and B7-H3 CAR-T cell (BB-Z-PD28) co-expressing the PD1-CD28 molecule have good similar proliferation abilities; as a control, B7-H3 CAR T cell (Del-Z) lacking intracellular signal function has no effective cell proliferation.

Figure 6:
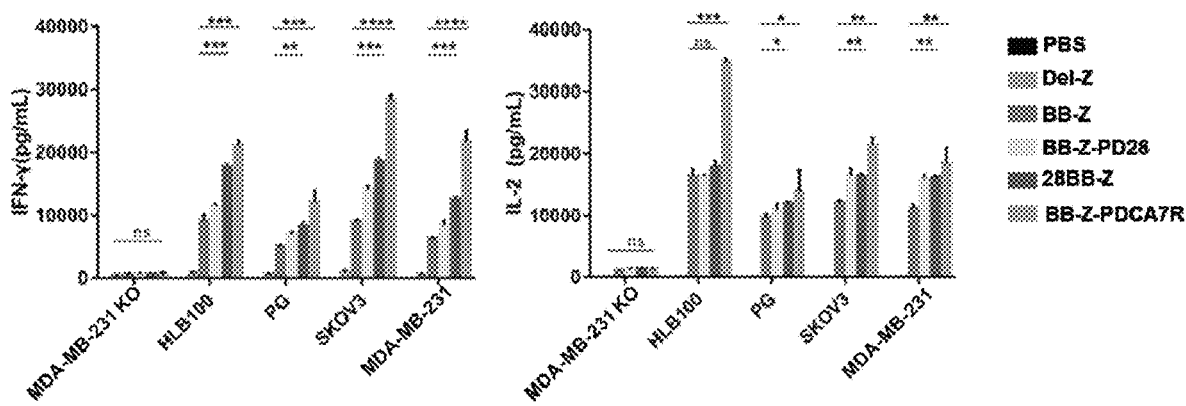

FIG. 6: different structures of CAR-T cells targeting B7-H3 respond to the secretion of cytokines from target tumor cells. The CAR-T cells of different structures produced different levels of cytokine (IL-2, IFN-r) secretion responses after specifically recognizing and activating B7-H3-positive tumor cells. MDA-MB-231-H3KO is a breast cancer cell that is negative after B7-H3 knockout and is used as a negative target cell control, and PBS is a blank control.

Figure 7:
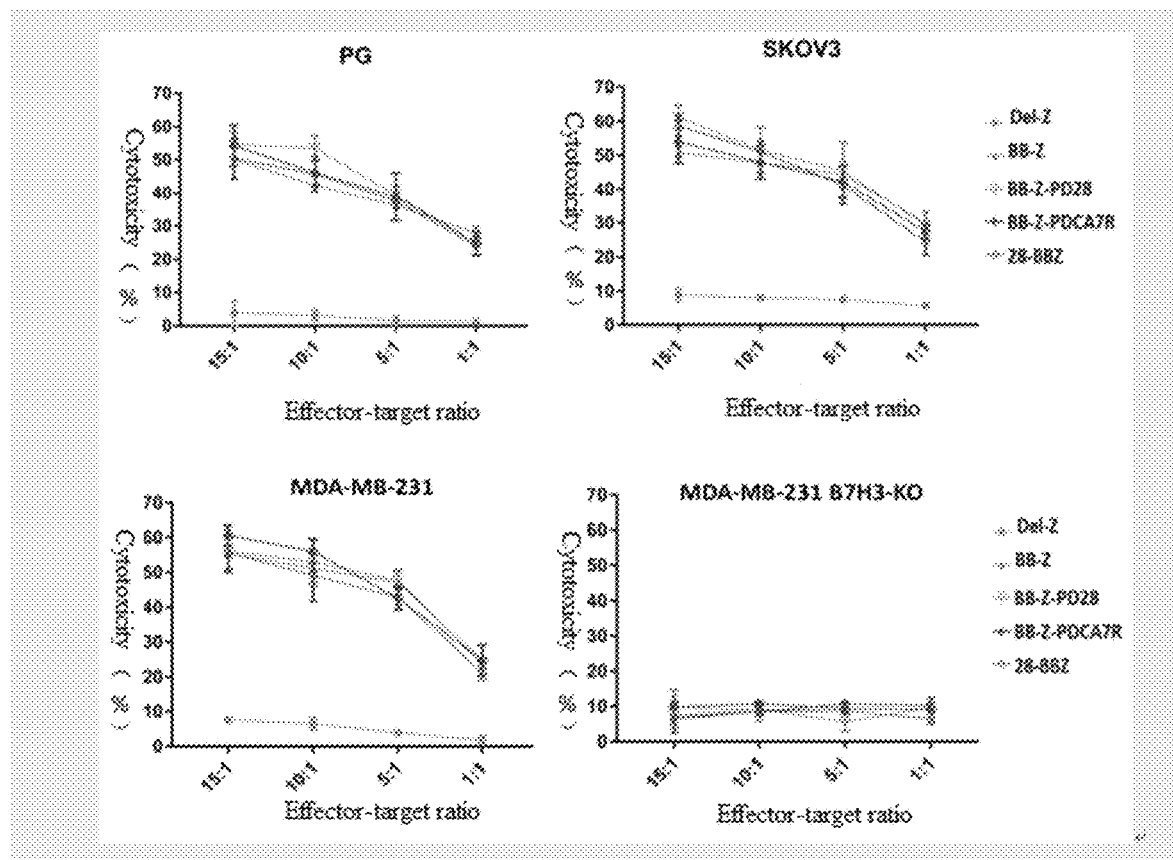

FIG. 7: in vitro specific killing of target tumor cells by B7-H3 CAR-T cells of different structures. Different structures of CAR-T cells targeting B7-H3 are respectively incubated with target tumor cells (lung cancer PG cells, ovarian cancer SKOV3 cells, or breast cancer MDA-MB-231 cells) at a certain effector-target ratio, and then tested for their killing functions. Except that the B7-H3 CAR T cell (Del-Z) lacking complete CD3ξ function has no effective killing effect, all other CAR-T cells have similar killing functions. MDA-MB-231-B7H3KO is a breast cancer cell that is negative after B7-H3 knockout. The B7-H3 CAR-T cells of different structures lack the killing function on it, confirming that the B7-H3 CAR-T cells have specificity on B7-H3 target antigens.

Figure 8:
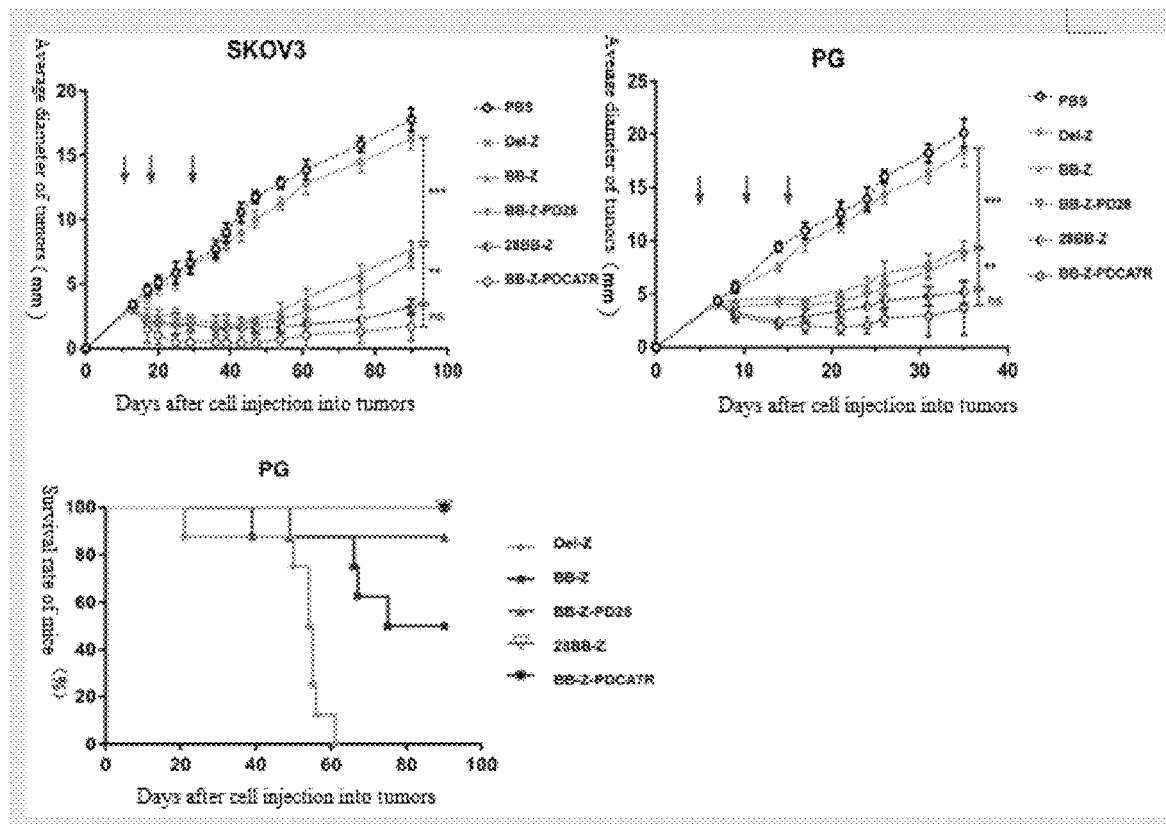

FIG. 8: CAR-T cell therapy targeting B7-H3 with different structures can effectively inhibit the growth of tumors in mouse subcutaneous tumor models (ovarian cancer, or lung cancer). In the mouse subcutaneous models of ovarian cancer or lung cancer, the B7-H3 CAR-T cells of different structures are subjected to intravenous injection therapy. Except that the B7-H3 CAR T cell (Del-Z) lacking complete CD3 as a control cannot inhibit tumor growth, various other B7-H3 CAR-T cells can effectively inhibit tumor growth.

Figure 9:
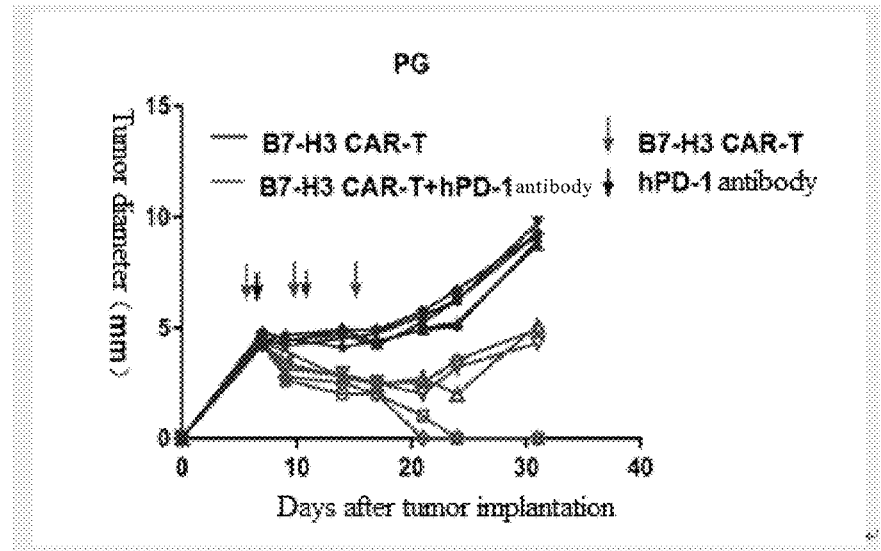

FIG. 9: the combination of the B7-H3 CAR-T cell and the anti-PD-1 antibody can improve anti-tumor efficacy. In a mouse lung cancer PG model, the B7-H3 CAR-T cell is used alone, or the B7-H3 CAR-T cell is combined with the anti-PD-1 antibody for intravenous injection therapy, and the effect of therapy is evaluated by monitoring tumor size.

FIG. 10 shows the killing effects of CAR-T cells constructed by humanized single-chain antibodies with different affinities on target cells. After humanization, single-chain antibodies formed by different combinations of light chains and heavy chains have different antibody affinities. The CAR-T cells constructed based on these single-chain antibodies with different affinities include B7H3-CAR-T-ori (CAR-T constructed with non-humanized sequences), and CAR-T cells (B7H3 CART-H2L2, B7H3 CART-H2L1, B7H3 CART-H1L2, B7H3 CART-L2H2) constructed with different combinations of sequences after humanization. After the B7H3 CAR-T cells of different combinations are incubated with colon cancer LOVO cells (8 hours), their killing effect and cytokine secretion (IL-2, IFN-γ) are tested.

Figure 1:
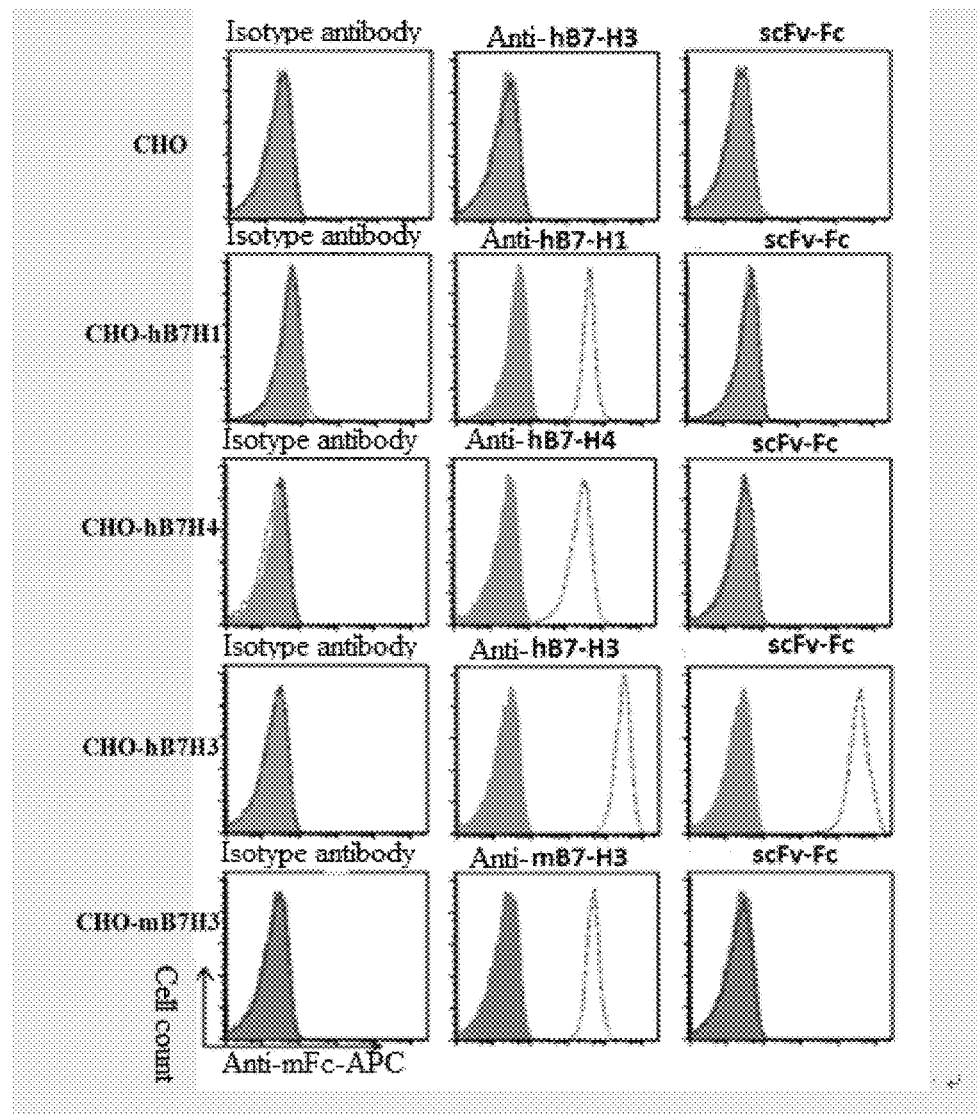
FIG. 1: An anti-human B7-H3 monoclonal antibody and single-chain antibody (scFv) thereof have specific binding ability to B7-H3. Anti-B7 family monoclonal antibodies and anti-human B7-H3 single-chain antibody protein (scFv) are used to stain CHO cells stably expressing human hB7-H1, hB7-H4, hB7-H3 and murine mB7-H3 of B7 family molecules, using mouse IgG antibody as isotype antibody control (isotope), flow cytometry shows that B7-H3 monoclonal antibody and the single-chain antibody protein (scFv) thereof can specifically bind to B7-H3.
Figure 2:
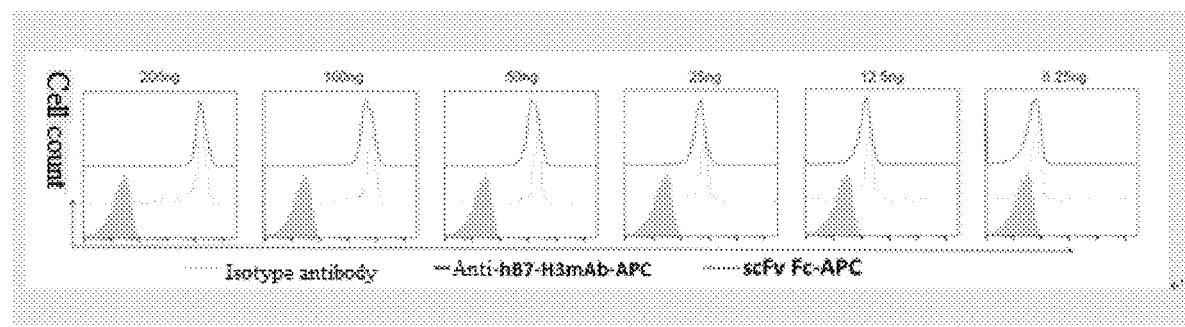
FIG. 2: an anti-human B7-H3 single-chain antibody and monoclonal antibody thereof have similar specific binding ability to B7-H3. Anti-human B7-H3 monoclonal antibody or anti-human B7-H3 single-chain antibody at different concentrations were respectively used to stain CHO cells stably expressing human B7-H3. Flow cytometry shows that the anti-human B7-H3 monoclonal antibody and single-chain antibody (scFv) thereof have basically similar ability to specifically bind to B7-H3.

FIG. 11: FIG. 11-1, the humanized B7-H3 CAR-T cells (B7H3 CART-H2L2) kill colon cancer LOVO cells in vitro, and the killing effect and cytokine secretion are tested; FIG. 11-2, anti-tumor effects of the humanized B7-H3 CAR-T cells in mouse colon cancer tumor models.

Figure 12:
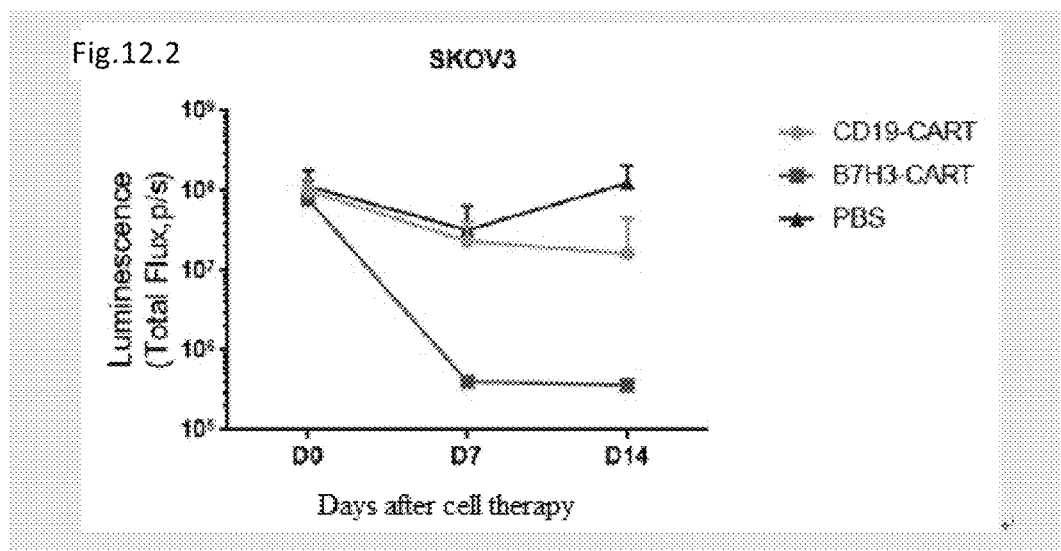

FIG. 12: FIG. 12-1, the humanized B7-H3 CAR-T cells (B7H3 CART-H2L2) kill ovarian cancer SKOV3 cells in vitro, and the killing effect and cytokine secretion are tested; FIG. 12-2, anti-tumor effects of the humanized B7-H3 CAR-T cells in mouse ovarian cancer tumor models.

Figure 13:
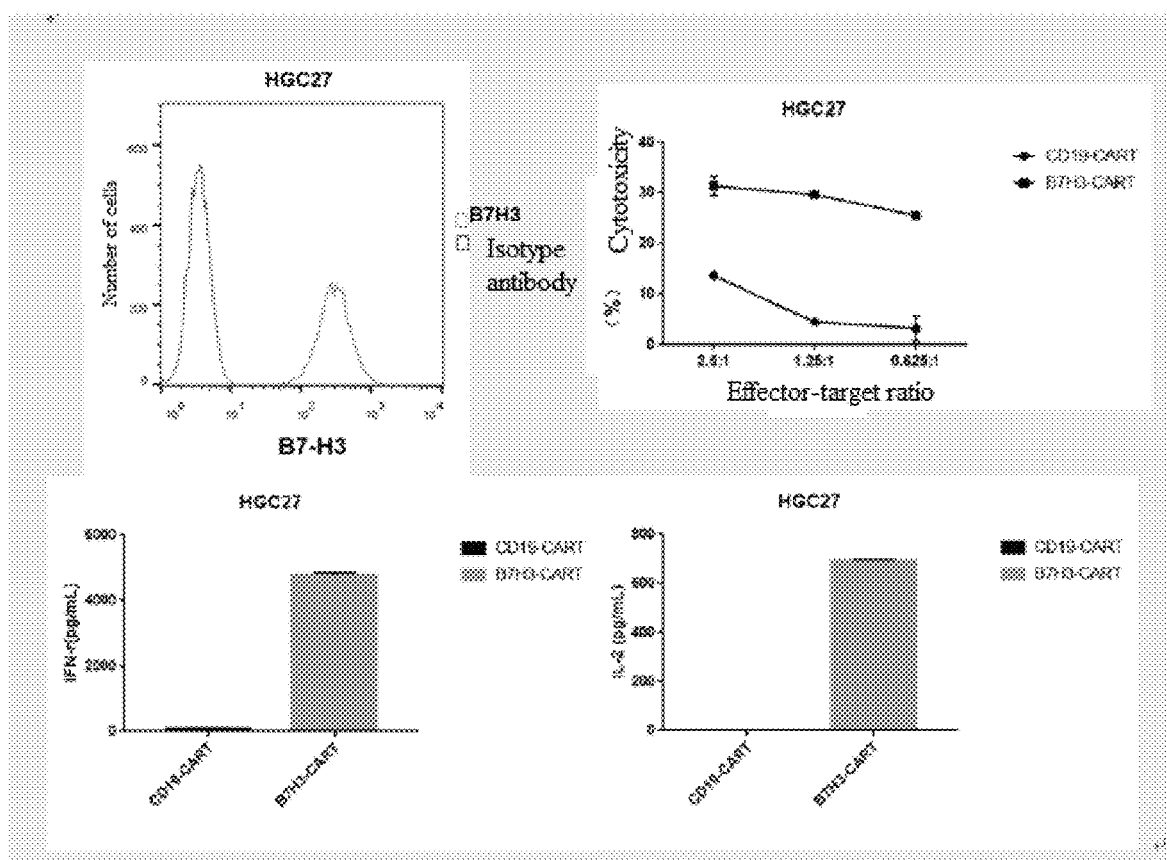

FIG. 13: the humanized B7-H3 CAR-T cells (B7H3 CART-H2L2) kill gastric cancer HGC27 cells in vitro, and the killing effect and cytokine secretion are tested.

Figure 14:
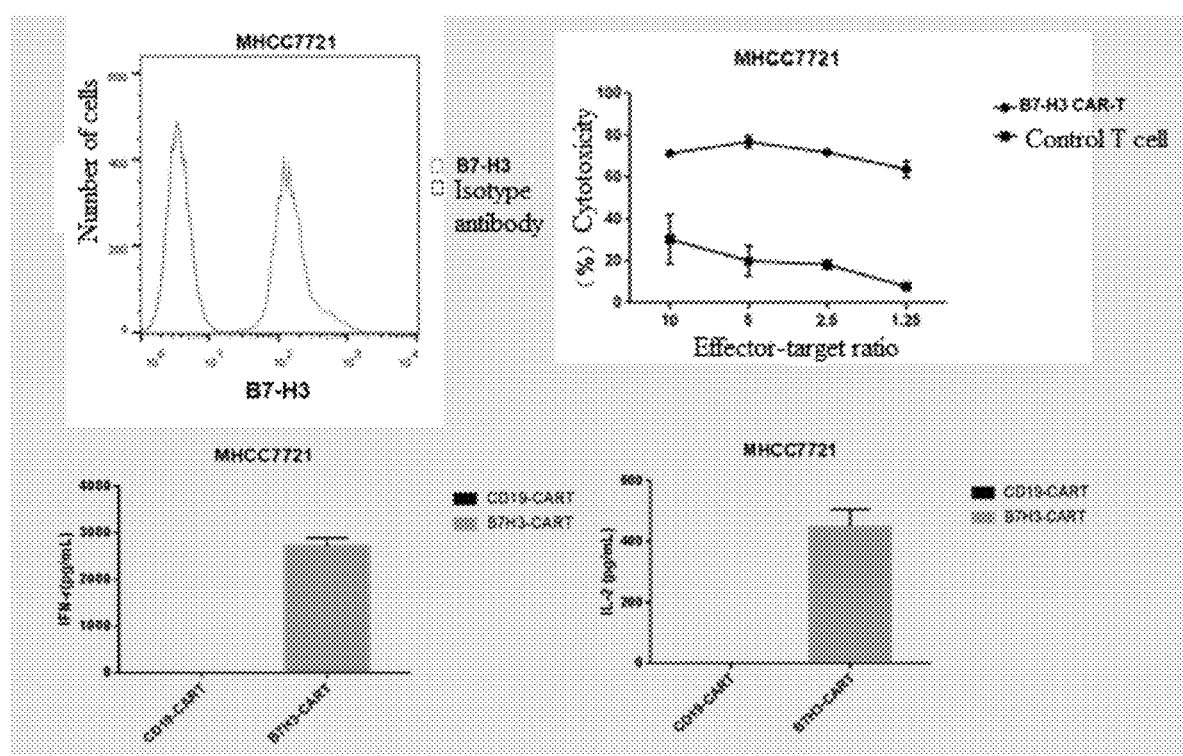

FIG. 14: the humanized B7-H3 CAR-T cells (B7H3 CART-H2L2) kill liver cancer MHCC7721 cells in vitro, and the killing effect and cytokine secretion are tested.

Figure 15:
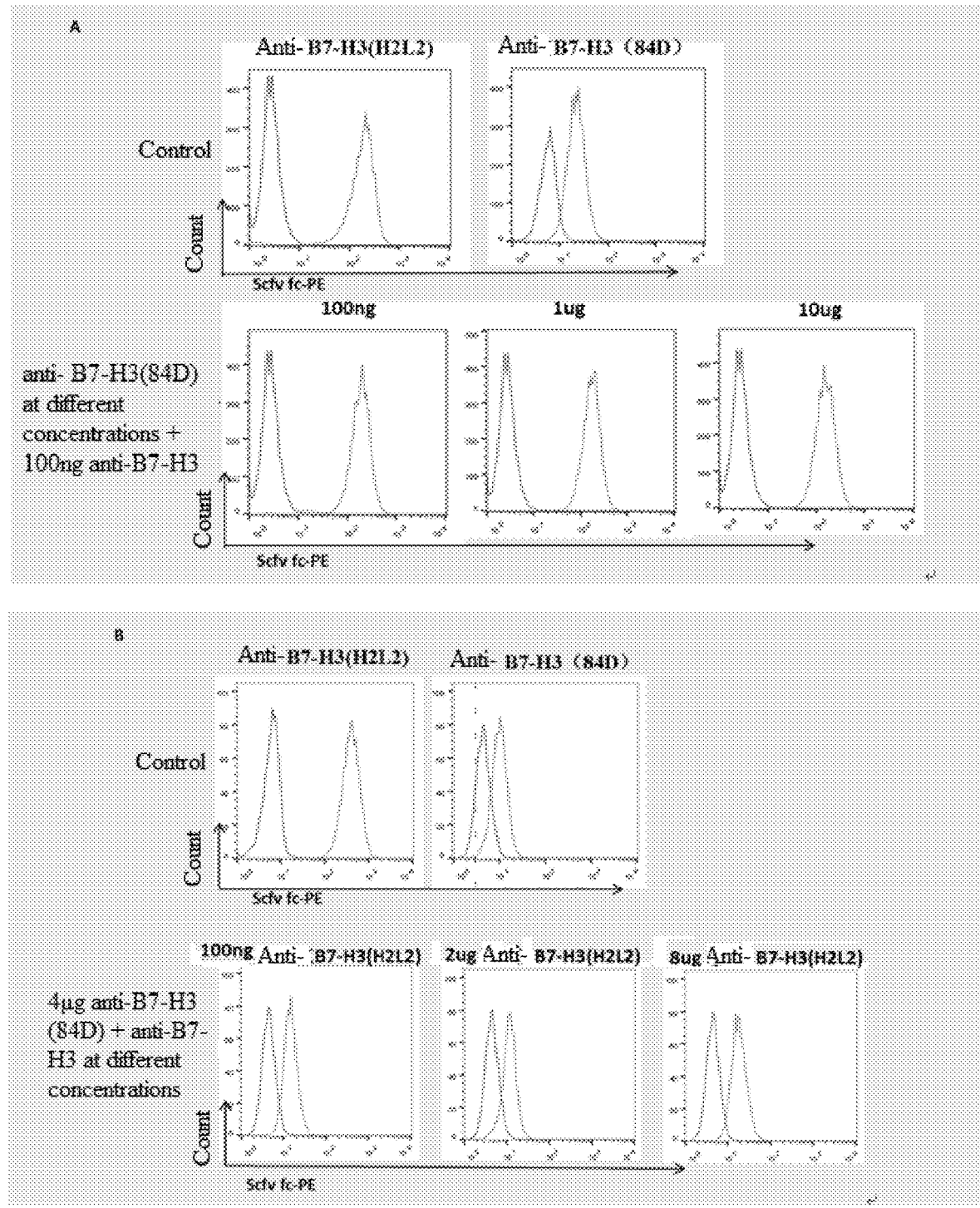

FIG. 15: competitive binding experiment of anti-B7-H3 single-chain antibody (H2L2) and anti-B7-H3 single-chain antibody (MGA271, 84D). The results show that the anti-B7-H3 single-chain antibody H2L2 and the 84D single-chain antibody do not compete for binding, and the two bind to different epitopes on the B7-H3 molecule.

DETAILED DESCRIPTION OF EMBODIMENTS

Through extensive and in-depth research and extensive screening, the inventors have unexpectedly developed for the first time a class of antibodies with high specificity and high affinity for B7-H3 and chimeric antigen receptor immune cells with high specificity based on the antibodies. Specifically, the present invention has unexpectedly obtained anti-B7-H3 monoclonal antibodies with extremely excellent affinity and specificity, and has obtained humanized antibodies based on the antibodies. The antibodies of the present invention can bind to B7-H3 antigens with high specificity, and having high affinity (with excellent Ka(1/Ms), Kd(1/s) and KD(M) based on measurement). The antibodies of the present invention and their corresponding chimeric antigen receptor immune cells can specifically target tumor cells that are B7-H3-positive or expressed or highly expressed B7-H3, having excellent tumor killing effects, but having no killing ability to normal cells. The present invention is completed on the basis of this.

Terms

In order to understand the present disclosure more easily, some terms are first defined. As used in this application, unless expressly stated otherwise herein, each of the following terms shall have the meaning given below. Other definitions are stated throughout the application.

The term "about" may refer to a value or composition within an acceptable error range of a particular value or composition determined by a person of ordinary skill in the art, which will depend in part on how the value or composition is measured or determined.

As used herein, "chimeric antigen receptor (CAR)" is a fusion protein, including an extracellular domain capable of binding to an antigen, a transmembrane domain derived from a different polypeptide from the extracellular domain, and at least one intracellular domain. The "chimeric antigen receptor (CAR)" is also known as "chimeric receptor", "T-body" or "chimeric immune receptor (CIR)". The "extracellular domain capable of binding to an antigen" refers to any oligopeptide or polypeptide capable of binding to a certain antigen. The "intracellular domain" refers to any oligopeptide or polypeptide known as a domain that transmits a signal to activate or inhibit a biological process in a cell.

As used herein, "domain" refers to a region in a polypeptide that is independent of other regions and folded into a specific structure.

As used herein, "tumor antigen" refers to a biological molecule with antigenicity, the expression of which causes cancer.

As used herein, "single-chain variable fragment (ScFv)" refers to a single-chain polypeptide derived from an antibody, which retains the ability to bind to an antigen. An example of ScFv includes an antibody polypeptide formed by recombinant DNA technology, and Fv regions of immunoglobulin heavy chain (H chain) and light chain (L chain) fragments therein are connected via a spacer sequence. Various methods of modifying ScFv are known to a person skilled in the art.

As used herein, the terms "administration" and "treatment" refer to the application of exogenous drugs, therapeutic agents, diagnostic agents or compositions to animals, humans, subjects, cells, tissues, organs, or biological fluids. The "administration" and "treatment" can refer to treatment, pharmacokinetics, diagnosis, research, and experimental methods. The treatment of cells includes contact between reagents and cells, contact between reagents and fluids, and contact between fluids and cells. The "administration" and "treatment" also mean treatment by reagents, diagnosis, binding compositions, or by another cells in vitro and ex vivo. When the "treatment" is applied to humans, animals or research subjects, it refers to treatment, prevention or preventive measures, research and diagnosis; including contact between anti-human B7-H3 antibodies and humans or animals, subjects, cells, tissues, physiological compartments or physiological fluids.

As used herein, the term "treatment" refers to the administration of an internal or external therapeutic agent, including any one of the anti-human B7-H3 antibodies of the present invention and a composition thereof, to a patient who has one or more disease symptoms, and it is known that the therapeutic agent has a therapeutic effect on these symptoms. Generally, the patient is administered in an amount (therapeutically effective dose) of a therapeutic agent effective to alleviate one or more disease symptoms.

As used herein, the term "optional" or "optionally" means that the event or situation described later can occur but does not have to occur. For example, "optionally including 1-3 antibody heavy chain variable regions" means that the antibody heavy chain variable region of a specific sequence may have but does not have to be, and it can be 1, 2, or 3. The "sequence identity" in the present invention refers to when optimally aligned and compared, the degree of identity between two nucleotide sequences or two amino acid sequences with appropriate mutations such as substitutions, insertions or deletions. The sequence identity between the sequence described in the present invention and identical sequence thereof may be at least 85%, 90% or 95%, preferably at least 95%. Non-limiting examples include 85%, 86%, 87%, 88%, 89%, 90%, 91%, 92%, 93%, 94%, 95%, 96%, 97%, 98%, 99%, and 100%.

B7-H3

The human B7-H3 molecule is a member of the B7 family, and is an I-type transmembrane protein with 506 amino acids and a molecular weight of 110 kDa. The human B7-H3 gene is first cloned from a cDNA library derived from human dendritic cells. Because its structure is similar to B7 family genes, it is named B7 Homolog3, or B7-H3 for short. The B7-H3 protein is an I-type transmembrane protein with an IgC or IgV-like domain outside the cell and a highly variable signal domain inside the cellexpressed by the guidance of a signal peptide, and has 20%-27% of homology with other members of the B7 family in amino acid sequence.

The initial discovery of B7-H3 mainly focuses on immunological studies, but in different studies, B-H3 has not only positive costimulatory activation for T cells, but also different reports of immunosuppressive functions, so its function is not yet clear. Studies have reported that B7-H3 molecules can co-stimulate the proliferation of $CD4^+$ T cells and $CD8^+$ T cells, enhance the induction of T cell immune killing response, and selectively stimulate the secretion of IFN-γ, IL-8, TNF-α and IL-10 and the like. More follow-up studies have proved that B7-H3 can negatively regulate the activation of T cells, and inhibit the activation of $CD4^+$ T cells and the secretion of corresponding cytokines such as IFN-γ and IL-4. At the same time, B7-H3 may also participate in the function of Treg to inhibit DC activation and present antigens.

The B7-H3 protein is not expressed or expressed extremely low in normal tissues and cells, but highly expressed in a variety of tumor tissues, and is related to tumor progression, poor patient prognosis and poor clinical outcome. In various studies, it is found that B7-H3 is expressed in various tumor tissues of patients with non-small cell lung cancer, prostate cancer, melanoma, breast cancer and pancreatic cancer. Moreover, the high expression of B7-H3 is positively correlated to the lymph node metastasis or bone metastasis of related tumors, tumor treatment resistance, postoperative progression and recurrence, and patient mortality. Therefore, the B7-H3 molecule can be used as a new solid tumor targeting molecule.

PD-1 Extracellular Fragment

The PD-1 extracellular fragment is an extracellular fragment of a PD-1 molecule:

(SEQ ID NO: 32)
PGWFLDSPDRPWNPPTFSPALLVVTEGDNATFTCSFSNTSESFVLNWYR

MSPSNQTDKLAAFPEDRSQPGQDCRFRVTQLPNGRDFHMSVVRARRNDS

GTYLCGAISLAPKAQIKESLRAELRVTERRAEVPTAH

Antibody

As used herein, the term "antibody" refers to an immunoglobulin, with a tetrapeptide chain structure composed of two identical heavy chains and two identical light chains connected by interchain disulfide bonds. The amino acid composition and sequence of heavy chain constant regions of immunoglobulins are different, so their antigenicities are also different. Accordingly, the immunoglobulins can be divided into five classes, or isotypes of the immunoglobulins, namely IgM, IgD, IgG, IgA and IgE. The corresponding heavy chains are μ chain, δ chain, γ chain, α chain, and E chain, respectively. The same class of Ig can be divided into different subclasses according to the difference in the amino acid composition of hinge regions and the number and position of heavy chain disulfide bonds. For example, IgG can be divided into IgG1, IgG2, IgG3, and IgG4. The light chain is divided into a κ chain or a λ chain according to the difference of the constant region. Each of the five classes of Ig can have a κ chain or a λ chain. The subunit structures and three-dimensional structures of different classes of immunoglobulins are well known to a person skilled in the art.

The antibody light chain of the present invention may further include a light chain constant region, and the light chain constant region includes a humanized or murine κ or λ, chain or variant thereof.

In the present invention, the antibody heavy chain of the present invention may further include a heavy chain constant region, and the heavy chain constant region includes humanized or murine IgG1, IgG2, IgG3, IgG4 or variant thereof. The sequence of about 110 amino acids near the N-terminals of the antibody heavy and light chains varies greatly and is a variable region (Fv region); and the sequence of remaining amino acids near the C-terminal is relatively stable and is a constant region. The variable region includes 3 hypervariable regions (HVR) and 4 framework regions (FR) with relatively conservative sequences. The three hypervariable regions determine the specificity of the antibody, and are also known as complementary determining regions (CDR). Each light chain variable region (LCVR) and heavy chain variable region (HCVR) is composed of 3 CDR regions and 4 FR regions, and their sequence from the amino terminal to the carboxy terminal is: FR1, CDR1, FR2, CDR2, FR3, CDR3 and FR4. The 3 CDR regions of the light chain refer to LCDR1, LCDR2 and LCDR3; and the 3 CDR regions of the heavy chain refer to HCDR1, HCDR2 and HCDR3.

The antibodies of the present invention include murine antibodies, chimeric antibodies, and humanized antibodies, preferably humanized antibodies. The term "murine antibody" in the present invention is an anti-human B7-H3 monoclonal antibody prepared according to the knowledge and skills in the art. During the preparation, the test subject is injected with the B7-H3 antigen, and then hybridomas expressing antibodies with the desired sequence or functional properties are isolated. In a preferred embodiment of the present invention, the murine B7-H3 antibody or antigen binding fragment thereof may further include a light chain constant region of a murine κ or λ chain or variant thereof, or further include a heavy chain constant region of murine IgG1, IgG2, IgG3 or variant thereof.

The term "chimeric antibody" is an antibody formed by fusing a variable region of a murine antibody with a constant region of a human antibody, which can reduce the immune response induced by the murine antibody.

The term "humanized antibody", also known as CDR-grafted antibody, refers to the transplantation of a mouse CDR sequence into a human antibody variable region framework, that is, an antibody produced in different types of human germline antibody framework sequences. The humanized antibody can overcome the heterogeneous reaction induced by the chimeric antibody carrying a large amount of murine protein components. Such framework sequences can be obtained from public DNA databases or published references that include antibody gene sequences in various germ lines. In order to avoid the decrease of immunogenicity and the resulting decrease in activity, the human antibody variable region framework sequence can be subjected to minimal reverse mutations or back mutations to maintain its activity.

The term "antigen binding fragment of an antibody" (or "antibody fragment" for short) refers to one or more fragments of an antibody that retain the ability to specifically bind to an antigen (for example, B7-H3). It has been shown that full-length fragments of an antibody can be used to perform the antigen binding function of the antibody. Examples of the binding fragment contained in the term "antigen binding fragment of an antibody" include:
  (i) Fab fragment, a monovalent fragment consisting of $V_L$, $V_H$, CL and CH1 domains;
  (ii) F(ab')$_2$ fragment, a bivalent fragment containing two Fab fragments connected by a disulfide bridge on a hinge region;
  (iii) Fd fragment consisting of $V_H$ and CH1 domains;
  (iv) Fv fragment consisting of $V_H$ and $V_L$ domains of a single arm of an antibody.

The Fv antibody contains a heavy chain variable region and a light chain variable region, but does not have a constant region, and has a minimum antibody fragment with all antigen binding sites. Generally, the Fv antibody further contains a polypeptide linker between the $V_H$ and $V_L$ domains, and can form a structure required for antigen binding.

The term "CDR" refers to one of the six hypervariable regions in the variable domain of an antibody that mainly contribute to antigen binding. One of the most common definitions of the 6 CDRs is provided by Kabat E. A et al. in (1991) Sequences of proteins of immunological interest. NIH Publication 91-3242).

The term "epitope" or "antigenic determinant" refers to a site on an antigen where an immunoglobulin or antibody specifically binds (for example, a specific site on a B7-H3 molecule). The epitope usually includes at least 3, 4, 5, 6, 7, 8, 9, 10, 11, 12, 13, 14, or 15 continuous or discontinuous amino acids in a unique spatial conformation.

The terms "specific binding", "selective binding", "selectively bind" and "specifically bind" refer to the binding of an antibody to an epitope on a predetermined antigen. Generally, the antibody binds with an affinity (KD) of about less than $10^{-7}$ M, for example, about less than $10^{-8}$ M, $10^{-9}$ M, or $10^{-10}$ M or less.

The term "competitive binding" refers to an antibody that recognizes the same epitope (also called an antigenic determinant) or a part of the same epitope on the extracellular region of human B7-H3 as the monoclonal antibody of the present invention and binds to the antigen. The antibody that binds to the same epitope as the monoclonal antibody of the present invention refers to an antibody that recognizes and binds to the amino acid sequence of human B7-H3 recognized by the monoclonal antibody of the present invention.

The term "KD" or "Kd" refers to a dissociation equilibrium constant of a specific antibody-antigen interaction. Generally, the antibody of the present invention binds to B7-H3 with a dissociation equilibrium constant (KD) of less than about $10^{-7}$ M, for example, less than about $10^{-8}$ M, $10^{-9}$ M, $10^{-10}$ M or less, as measured in a BIACORE instrument by using surface plasmon resonance (SPR) technology.

As used herein, the term "antigenic determinant" refers to three-dimensional sites that are discontinuous on the antigen and are recognized by the antibody or antigen binding fragment of the present invention.

The present invention includes not only complete antibodies, but also fragments of immunologically active antibodies or fusion proteins formed by antibodies and other sequences. Therefore, the present invention further includes fragments, derivatives and analogs of the antibodies.

In the present invention, the antibodies include murine, chimeric, humanized, or fully human antibodies prepared by the technologies well known to a person skilled in the art. Recombinant antibodies, such as chimeric and humanized monoclonal antibodies, including human and non-human parts, can be prepared using DNA recombinant technology well known in the art.

As used herein, the term "monoclonal antibody" refers to an antibody secreted by a clone derived from a single cell. The monoclonal antibody is highly specific and is directed against a single epitope. The cells may be eukaryotic, prokaryotic, or phage clonal cell strains.

In the present invention, the antibodies may be monospecific, bispecific, trispecific, or more multispecific.

In the present invention, the antibody of the present invention further includes its conservative variants, which means that compared with the amino acid sequence of the antibody of the present invention, at most 10, preferably at most 8, more preferably at most 5, and most preferably at most 3 amino acids are substituted by amino acids with similar or similar properties to form a polypeptide. These conservative variant polypeptides are best produced by amino acid substitution according to Table A.

TABLE A

| Initial residue | Representative substitution | Preferred substitution |
| --- | --- | --- |
| Ala (A) | Val; Leu; Ile | Val |
| Arg (R) | Lys; Gln; Asn | Lys |
| Asn (N) | Gln; His; Lys; Arg | Gln |
| Asp (D) | Glu | Glu |
| Cys (C) | Ser | Ser |
| Gln (Q) | Asn | Asn |
| Glu (E) | Asp | Asp |
| Gly (G) | Pro; Ala | Ala |
| His (H) | Asn; Gln; Lys; Arg | Arg |
| Ile (I) | Leu; Val; Met; Ala; Phe | Leu |
| Leu (L) | Ile; Val; Met; Ala; Phe | Ile |
| Lys (K) | Arg; Gln; Asn | Arg |
| Met (M) | Leu; Phe; Ile | Leu |
| Phe (F) | Leu; Val; Ile; Ala; Tyr | Leu |
| Pro (P) | Ala | Ala |
| Ser (S) | Thr | Thr |
| Thr (T) | Ser | Ser |
| Trp (W) | Tyr; Phe | Tyr |
| Tyr (Y) | Trp; Phe; Thr; Ser | Phe |
| Val (V) | Ile; Leu; Met; Phe; Ala | Leu |

Human B7-H3 Specific Antibody

The present invention provides an anti-human B7-H3 antibody (hereinafter referred to as B7-H3 antibody). Specifically, the present invention provides a high-specificity and high-affinity antibody against B7-H3, including a heavy chain and a light chain, the heavy chain containing a heavy chain variable region ($V_H$) amino acid sequence, and the light chain containing a light chain variable region ($V_L$) amino acid sequence. The B7-H3 antibody of the present invention enhances the anti-tumor effect of T cells by stimulating the antigen-specific T cells response, thereby maximizing the patient's own immune system response to tumors and achieving the purpose of killing tumor cells.

Preferably, the respective CDRs of the heavy chain variable region ($V_H$) amino acid sequence and the light chain variable region ($V_L$) amino acid sequence are selected from the group consisting of:

a1) SEQ ID NO: 1;
a2) SEQ ID NO: 2;
a3) SEQ ID NO: 3;
a4) SEQ ID NO: 4;
a5) SEQ ID NO: 5;
a6) SEQ ID NO: 6;
a7) SEQ ID NO: 7;
a8) SEQ ID NO: 8;
a9) SEQ ID NO: 9;
a10) SEQ ID NO: 10;
a11) SEQ ID NO: 11;
a12) SEQ ID NO: 12;
a13) SEQ ID NO: 13;
a14) SEQ ID NO: 14;
a15) SEQ ID NO: 15;
a16) SEQ ID NO: 16;
a17) SEQ ID NO: 17;
a18) SEQ ID NO: 18

Any one of the abovementioned amino acid sequences includes a sequence in which at least one (for example, 1-5, 1-3, preferably 1-2, more preferably 1) amino acid is added, deleted, modified and/or substituted and that has B7-H3 binding affinity.

In another preferred example, the sequence in which at least one (for example, 1-5, 1-3, preferably 1-2, more preferably 1) amino acid is added, deleted, modified and/or substituted is preferably an amino acid sequence having a homology of at least 80%, preferably at least 85%, more preferably at least 90%, and most preferably at least 95%.

The antibody of the present invention may be a double-chain or single-chain antibody, and may be selected from animal antibodies, chimeric antibodies and humanized antibodies, more preferably humanized antibodies and human-animal chimeric antibodies, and more preferably fully humanized antibodies.

The antibody derivatives of the present invention may be single-chain antibodies and/or antibody fragments, such as: Fab, Fab', (Fab')$_2$, or other antibody derivatives known in the art, as well as IgA, IgD, IgE, IgG and IgM antibodies or any one or more of antibodies of other subtypes.

The animal is preferably a mammal, such as murine.

The antibody of the present invention may be a murine antibody, chimeric antibody, humanized antibody, or CDR grafted and/or modified antibody targeting human B7-H3.

In a preferred embodiment of the present invention, any one or more of the sequences shown in SEQ ID NOs: 1, 2, 3, 4, 5, 6, 7, 8 and 9, or sequences thereof in which at least one amino acid is added, deleted, modified and/or substituted and that have B7-H3 binding affinity, are within the CDR region of the heavy chain variable region (VH).

In a preferred embodiment of the present invention, any one or more of the sequences shown in SEQ ID NOs: 10, 11, 12, 13, 14, 15, 16, 17 and 18, or sequences thereof in which at least one amino acid is added, deleted, modified and/or substituted and that have B7-H3 binding affinity, are within the CDR region of the light chain variable region ($V_L$).

In a more preferred embodiment of the present invention, $V_H$ CDR1, CDR2, and CDR3 are independently selected from any one or more of the sequences shown in SEQ IDs NOs: 1, 2, 3, 4, 5, 6, 7, 8 and 9, or sequences thereof in which at least one amino acid is added, deleted, modified and/or substituted and that have B7-H3 binding affinity; and $V_L$, CDR1, CDR2, and CDR3 are independently selected from any one or more of the sequences shown in SEQ ID NOs: 10, 11, 12, 13, 14, 15, 16, 17 and 18, or sequences thereof in which at least one amino acid is added, deleted, modified and/or substituted and that have B7-H3 binding affinity.

In the abovementioned content of the present invention, the number of the added, deleted, modified and/or substituted amino acids is preferably not more than 40% of the total number of amino acids in the initial amino acid sequence, more preferably not more than 35%, more preferably 1-33%, more preferably 5-30%, more preferably 10-25%, and more preferably 15-20%.

In the present invention, the number of the added, deleted, modified and/or substituted amino acids is usually 1, 2, 3, 4 or 5, preferably 1-3, more preferably 1-2, and most preferably 1.

Preparation of Antibodies

Any method suitable for producing monoclonal antibodies can be used to produce the B7-H3 antibody of the present invention. For example, animals can be immunized with linked or natural B7-H3 proteins or fragments thereof. Suitable immunization methods can be used, including adjuvant, immunostimulant, and repeated booster immunizations, and one or more of the methods can be used.

Any suitable form of B7-H3 can be used as an immunogen (antigen) to produce non-human antibodies specific to B7-H3 and screen the biological activity of the antibodies. The immunogen can be used alone or used with one or more immunogenicity enhancers known in the art. The immunogen can be purified from natural sources or produced in genetically modified cells. DNA encoding the immunogen may be genomic or non-genomic (e.g., cDNA) in source. A suitable genetic vector can be used to express the DNA encoding the immunogen, and the vector includes but is not limited to adenoviral vectors, baculoviral vectors, plasmids, and non-viral vectors.

An exemplary method for producing the B7-H3 antibody of the present invention is described in Example 1.

The humanized antibody may be selected from any kind of immunoglobulin, including IgM, IgD, IgG, IgA, and IgE. In the present invention, the antibody is an IgG antibody of an IgG1 or IgG4 subtype.

Likewise, any type of light chain can be used in the compound and method herein. Specifically, the κ or λ chain or variant thereof can be used in the compound and method of the present invention.

An exemplary method for humanizing the B7-H3 antibody of the present invention is described in Example 1.

The sequence of the DNA molecule of the antibody or fragment thereof of the present invention can be obtained by conventional technology, such as PCR amplification or genomic library screening etc. In addition, the coding sequences of different light chains and heavy chains can be fused together in different combinations to form single-chain antibodies. Optimized single-chain antibodies can be obtained by testing and analyzing the functions of single-chain antibodies modified by different combinations or different linkages.

Once a relevant sequence is obtained, other relevant sequences can be obtained on a large scale by recombination. This usually involves cloning into a vector, then transferring to a cell, and then isolating from the proliferated host cell by a conventional method to obtain the relevant sequences.

In addition, the relevant sequences can also be synthesized artificially, especially in the case that the fragments are short. Usually, a plurality of small fragments are first synthesized and then joined to obtain very long fragments. The DNA sequence can then be introduced into various existing DNA molecules (or such as vectors) and cells known in the art.

The term "nucleic acid molecule" refers to DNA molecules and RNA molecules. The nucleic acid molecule may be single-stranded or double-stranded, but preferably double-stranded DNA. When a nucleic acid is placed in a functional relationship with another nucleotide sequence, the nucleic acid is "effectively linked." For example, if a promoter or enhancer affects the transcription of a coding sequence, the promoter or enhancer is effectively linked to the coding sequence.

The term "vector" refers to a nucleic acid molecule capable of transporting another nucleic acid to which it has been linked. In one embodiment, the vector is a "plasmid", which refers to a circular double-stranded DNA loop to which an additional DNA fragment can be linked.

The present invention further relates to vectors containing the above-mentioned suitable DNA sequence and suitable promoter or control sequence. These vectors can be used to transform appropriate host cells to enable the host cells to express proteins.

The term "host cell" refers to a cell into which an expression vector has been introduced. The host cells may be prokaryotic cells, such as bacterial cells; or lower eukaryotic cells, such as yeast cells; or higher eukaryotic cells, such as plant or animal cells (e.g., mammalian cells).

The step of transforming host cells with recombinant DNA in the present invention can be performed by the technologies well known in the art. The obtained transformants can be cultured by conventional methods, and the transformants express polypeptides encoded by the genes of the present invention. Culture is carried out in a conventional medium under suitable conditions according to the used host cells.

Generally, the transformed host cells are cultured under conditions suitable for expression of the antibodies of the present invention. Then a conventional immunoglobulin purification step proceeds, to obtain the antibodies of the present invention by conventional isolation and purification means well known to a person skilled in the art, such as protein A-Sepharose, hydroxyapatite chromatography, gel electrophoresis, dialysis, ion exchange chromatography, hydrophobic chromatography, molecular sieve chromatography or affinity chromatography.

The obtained monoclonal antibodies can be identified by conventional means. For example, the binding specificity of the monoclonal antibodies can be measured by immunoprecipitation or binding assay in vitro (e.g., radioimmunoassay (RIA) or enzyme-linked immunosorbent assay (ELISA)).

Chimeric Antigen Receptors (CAR)

Chimeric antigen receptors (CARs) are composed of extracellular antigen recognition regions, usually scFv (single-chain variable fragment), transmembrane regions and intracellular costimulatory signal regions. CARs design goes through the following processes: the first-generation CARs have only one intracellular signal component CD3ζ or FcγRI molecule; because there is only one activation domain in a cell, it can only cause transient T cell proliferation and less cytokine secretion, but cannot provide long-term T cell proliferation signals and persistent anti-tumor effects in vivo, so it has not achieved good clinical effects; the second-generation CARs introduce a costimulatory molecule based on the original structure, such as CD28, 4-1BB, OX40, or ICOS; compared with the first-generation CARs, the function has been greatly improved, and the persistence of CAR-T cells and the ability to kill tumor cells are further enhanced; some new immunostimulatory molecules such as CD27 and CD134 are linked to the second-generation CARs in series to develop into third- and fourth-generation CARs.

The extracellular fragment of CARs can recognize a specific antigen, and then the intracellular domain transduces the signal to cause cell activation and proliferation, cytotoxicity lysis, and cytokine secretion, thereby eliminating target cells. Patient's autologous cells (or heterologous donors) are first isolated, activated and genetically modified to produce CAR immune cells, which are then injected into the same patient. In this way, the probability of suffering from graft-versus-host diseases is extremely low, and the antigens are recognized by immune cells in a non-MHC-restricted manner.

CAR-immune cell therapy has achieved a very high clinical response in the treatment of hematological malignancies. Such a high response cannot be achieved by any previous treatment means. It has triggered an upsurge of clinical research in the world.

Specifically, the chimeric antigen receptor (CAR) of the present invention includes an extracellular domain, a transmembrane domain, and an intracellular domain. The extracellular domain includes a target-specific binding component (also called an antigen binding domain). The intracellular domain includes a costimulatory signal transduction region and/or ζ chain portion. The costimulatory signal transduction region refers to a part of the intracellular domain that includes costimulatory molecules. The costimulatory molecules are cell surface molecules needed for effective response of lymphocytes to antigens, not antigen receptors or ligands thereof.

A linker can be incorporated between the extracellular domain and the transmembrane domain of the CAR, or between the cytoplasmic domain and the transmembrane domain of the CAR. As used herein, the term "linker" generally refers to any oligopeptide or polypeptide that functions to connect the transmembrane domain to the extracellular or cytoplasmic domain of a polypeptide chain. The linker may include 0-300 amino acids, preferably 2 to 100 amino acids and most preferably 3 to 50 amino acids.

When the CARs of the present invention are expressed in T cells, antigens can be recognized on the basis of the antigen binding specificity. When the CARs bind to associated antigens thereof, tumor cells will be affected, not grow, be dead or affected in other ways, and the patient's tumor burden is reduced or eliminated. The antigen binding domain is preferably fused with one or more intracellular domains from the costimulatory molecule and/or ζ chain. Preferably, the antigen binding domain is fused with the intracellular domain combined with the 4-1BB signal transduction domain and/or the CD3 signal domain.

As used herein, "antigen binding domain" and "single-chain antibody fragment" both refer to Fab fragments, Fab' fragments, F(ab')2 fragments, or single Fv fragments that have antigen binding activity. The Fv antibody contains a heavy chain variable region and a light chain variable region, but does not have a constant region, and has a minimum antibody fragment with all antigen binding sites. Generally, the Fv antibody further contains a polypeptide linker between the $V_H$ and $V_L$ domains, and can form a structure required for antigen binding. The antigen binding domain is usually scFv (single-chain variable fragment). The size of scFv is generally ⅙ that of a complete antibody. The single-chain antibody is preferably an amino acid chain sequence encoded by a nucleotide chain. As a preferred mode of the present invention, the scFv includes an antibody that specifically recognizes a highly expressed antigen B7-H3 of a tumor, preferably a single-chain antibody.

In the present invention, the scFv of the present invention further includes conservative variants thereof, which means that compared with the amino acid sequence of the scFv of the present invention, at most 10, preferably at most 8, more preferably at most 5, and most preferably at most 3 amino acids are substituted by amino acids with similar or similar properties to form a polypeptide.

In the present invention, the number of the added, deleted, modified and/or substituted amino acids is preferably not more than 40% of the total number of amino acids in the initial amino acid sequence, more preferably not more than 35%, more preferably 1-33%, more preferably 5-30%, more preferably 10-25%, and more preferably 15-20%.

In the present invention, the number of the added, deleted, modified and/or substituted amino acids is usually 1, 2, 3, 4 or 5, preferably 1-3, more preferably 1-2, and most preferably 1.

For the hinge region and the transmembrane region (transmembrane domain), the CAR can be designed to include a transmembrane domain fused to the extracellular domain of the CAR. In one embodiment, the transmembrane domain naturally associated with one of the domains in the CAR is used. In some examples, the transmembrane domain can be selected or modified by amino acid substitution to avoid binding such domains to the transmembrane domains of the same or different surface membrane proteins, thereby minimizing interaction with other members of the receptor complex.

In the present invention, the CAR of the present invention is described in the seventh aspect of the present invention.

Chimeric Antigen Receptor T Cell (CAR-T Cell)

As used herein, the terms "CAR-T cell", "CAR-T" and "CAR-T cell of the present invention" all refer to the CAR-T cell described in the seventh aspect of the present invention. The CAR-T cell of the present invention can target a tumor antigen (such as B7-H3).

After the CAR of the present invention is expressed, it will pass through the cell membrane and be located on the cell membrane.

The CAR-T cell has the following advantages over other T cell-based therapies: (1) the action process of the CAR-T cell is not restricted by MHC; (2) in view of the fact that many tumor cells express the same tumor antigen, once the construction of a CAR gene against one tumor antigen is completed, the CAR gene can be widely used; (3) the CAR can use both tumor protein antigens and glycolipid non-protein antigens, which expands the target range of the tumor antigens; (4) the use of patient's autologous cells reduces the risk of rejection; and (5) the CAR-T cell has immune memory function and can survive in vivo for a long time.

Chimeric Antigen Receptor NK Cell (CAR-NK Cell)

As used herein, the terms "CAR-NK cell", "CAR-NK" and "CAR-NK cell of the present invention" all refer to the CAR-NK cell described in the first aspect of the present invention. The CAR-NK cell of the present invention can target a tumor antigen (such as B7-H3).

Natural killer (NK) cells are a class of major immune effector cells that protect the body from virus infection and tumor cell invasion by non-antigen-specific ways. The engineered (gene modified) NK cell may obtain new functions, including the ability to specifically recognize tumor antigens and the enhanced anti-tumor cytotoxicity.

Compared with the autologous CAR-T cell, the CAR-NK cell further has the following advantages, for example: (1) directly killing tumor cells by releasing perforin and granzyme, but not killing normal cells in the body; (2) releasing a small amount of cytokines, thereby reducing the risk of cytokine storm; and (3) easily expanding in vitro and developing into "ready-made" products. Otherwise, it is similar to CAR-T cell therapy.

Exogenous T Cell Receptor

As used herein, the exogenous T cell receptor (TCR) refers to the TCR whose α chain and β chain are cloned from a tumor-reactive T cell through gene delivery technology and are exogenously transferred to the T cell by means of genetic engineering means, with lentivirus or retrovirus being used as vector.

T cells modified by exogenous TCR can specifically recognize and kill tumor cells. By optimizing the affinity of TCR to tumor-specific antigens, the affinity of T cells to tumors can be increased, and the anti-tumor effect can be improved.

Vector

A nucleotide sequence encoding a desired molecule can be obtained by a recombination method known in the art, for example, by screening a library from cells expressing genes, and obtaining a gene from a vector known to include the gene, or by directly isolating a gene from the cell and tissue containing the gene through a standard technology. Alternatively, the gene of interest can be produced synthetically.

The present invention further provides a vector into which an expression cassette of the present invention is inserted. Vectors derived from retroviruses such as lentiviruses are suitable tools to achieve long-term gene delivery, because they allow long-term and stable integration of transgenes and propagation in daughter cells. The lentiviral vectors have advantages over vectors derived from oncogenic retroviruses such as murine leukemia viruses, because they can transduce non-proliferating cells such as hepatocytes. They also have the advantage of low immunogenicity.

Briefly summarized, the expression cassette or nucleotide sequence of the present invention is usually operably linked to a promoter and incorporated into an expression vector. The vector is suitable for replication and integration of eukaryotic cell. A typical cloning vector contains a transcription and translation terminator that can be used to regulate the expression of a desired nucleotide sequence, an initial sequence, and a promoter.

The expression construct of the present invention can also be used for nucleic acid immunization and gene therapy by using standard gene delivery schemes. Methods of gene delivery are known in the art. See, for example, U.S. Pat. Nos. 5,399,346, 5,580,859, 5,589,466, which are hereby incorporated by reference in their entirety. In another embodiment, the present invention provides a gene therapy vector.

The nucleic acid can be cloned into many types of vectors. For example, the nucleic acid can be cloned into such vectors, which include, but are not limited to, plasmids, phagemids, phage derivatives, animal viruses, and cosmids. Specific vectors of interest include expression vectors, replication vectors, probe generation vectors, and sequencing vectors.

Further, the expression vectors can be provided to cells in the form of viral vectors. The viral vector technology is well known in the art and is described in, for example, Sambrook et al. (2001, Molecular Cloning: A Laboratory Manual, Cold Spring Harbor Laboratory, New York) and other virology and molecular biology manuals. Viruses that can be used as vectors include, but are not limited to, retroviruses, adenoviruses, adeno-associated viruses, herpes viruses, and lentiviruses. Generally, a suitable vector contains an origin of replication that functions in at least one organism, a promoter sequence, a convenient restriction enzyme site, and one or more optional markers (e.g., WO01/96584; WO01/29058; and U.S. Pat. No. 6,326,193).

Many virus-based systems have been developed for delivering gene into mammalian cells. For example, retroviruses provide a convenient platform for gene delivery systems. The selected gene can be inserted into a vector and packaged into a retrovirus particle by using a technology known in the art. The recombinant virus can then be isolated and transferred to an object cell in vivo or ex vivo. Many retrovirus systems are known in the art. In some embodiments, adenoviral vectors are used. Many adenoviral vectors are known in the art. In one embodiment, lentiviral vectors are used.

Additional promoter components, such as enhancers, can regulate the frequency of transcription initiation. Generally, these are located in a 30-110 bp region upstream of the initiation site, although it has recently been shown that many promoters also contain functional components downstream of the initiation site. The spacing between the promoter components is often flexible in order to maintain promoter functions when one component is inverted or moved relative to the other one. In a thymidine kinase (tk) promoter, the activity does not begin to decrease until that the spacing between promoter components can be increased by 50 bp. Depending on the promoter, it appears that individual components can act cooperatively or independently to initiate transcription.

An example of a suitable promoter is an immediate early cytomegalovirus (CMV) promoter sequence. The promoter sequence is a strong constitutive promoter sequence capable of driving high-level expression of any polynucleotide sequence operably linked thereto. Another example of a suitable promoter is an elongation growth factor-1α (EF-1α). However, other constitutive promoter sequences can also be used, including but not limited to simian virus 40 (SV40) early promoters, mouse mannary tumour virus (MMTV) and human immunodeficiency virus (HIV) long terminal repeat (LTR) promoters, MoMuLV promoters, avian leukemia virus promoters, Epstein-Barr virus immediate early promoters, Ruth sarcoma virus promoters, and human gene promoters, such as but not limited to actin promoters, myosin promoters, heme promoters and creatine kinase promoters. Further, the present invention should not be limited to the application of constitutive promoters. Inducible promoters are also considered part of the present invention. The use of an inducible promoter provides a molecular switch that can turn on expression of a polynucleotide sequence operably linked to the inducible promoter when such expression is desired, or turn off the expression when the expression is not desired. Examples of the inducible promoters include, but are not limited to, metallothionein promoters, glucocorticoid promoters, progesterone promoters and tetracycline promoters.

In order to evaluate the expression of a CAR polypeptide or part thereof, the expression vector introduced into the cell may also contain either or both of the optional marker gene or reporter gene, so as to identify and select an expression cell from a transfected or infected cell population sought through a viral vector. In other aspects, the optional marker can be carried on a single segment of DNA and used in a co-transfection procedure. Both the optional marker and reporter gene can be flanked by appropriate regulatory sequences to enable expression in the host cell. Useful optional markers include, for example, antibiotic resistance genes such as neo.

Reporter genes are used to identify potentially transfected cells and to evaluate the functionality of regulatory sequences. Generally, a reporter gene is a gene that does not exist in or is expressed by a receptor organism or tissue, and encodes a polypeptide whose expression is clearly indicated by some easily detectable properties such as enzyme activity. After the DNA is introduced into the receptor cell, the expression of the reporter gene is measured at an appropriate time. Suitable reporter genes may include genes encoding luciferase, β-galactosidase, chloramphenicol acetyltransferase, secreted alkaline phosphatase, or green fluorescent protein (e.g., Ui-Tei et al., 2000FEBS Letters 479:79-82). Suitable expression systems are well known and can be prepared by using known techniques or obtained commercially. Generally, a construct with a minimum of 5 flanking regions that shows the highest level of reporter gene expression is identified as a promoter. Such a promoter region can be linked to a reporter gene and used to evaluate the ability of a reagent to regulate the promoter-driven transcription.

Methods of introducing and expressing genes into cells are known in the art. In the content of the expression vector, the vector can be easily introduced into a host cell, for example, a mammalian, bacteria, yeast, or insect cell, by any method in the art. For example, the expression vector can be transferred into the host cell by physical, chemical or biological means.

Physical methods of introducing polynucleotides into host cells include calcium phosphate precipitation, lipofection, particle bombardment, microinjection, electroporation, etc. Methods of producing cells including vectors and/or exogenous nucleic acids are well known in the art. See, for example, Sambrook et al. (2001, Molecular Cloning: A Laboratory Manual, Cold Spring Harbor Laboratory, New York). The preferred method of introducing polynucleotides into host cells is calcium phosphate transfection.

Biological methods for introducing polynucleotides of interest into host cells include the use of DNA and RNA vectors. Viral vectors, especially retroviral vectors, have become the most widely used method of inserting genes into mammalian cells such as human cells. Other viral vectors can be derived from lentivirus, poxvirus, herpes simplex virus I, adenovirus, adeno-associated virus, etc. See, for example, U.S. Pat. Nos. 5,350,674 and 5,585,362.

Chemical means for introducing polynucleotides into host cells include colloidal dispersion systems, such as macromolecular complexes, nanocapsules, microspheres, and beads; and lipid-based systems, including oil-in-water emulsions, micelles, mixed micelles, and liposomes. Exemplary colloidal systems used as delivery vehicles in vitro and in vivo are liposomes (e.g., artificial membrane vesicles).

When a non-viral delivery system is used, an exemplary delivery vehicle is liposome. Lipid preparation are considerable to introduce nucleic acids into host cells (in vitro, ex vivo or in vivo). In another aspect, the nucleic acids can be associated with lipids. A lipid-associated nucleic acid can be encapsulated in the aqueous interior of a liposome, dispersed in the lipid bilayer of the liposome, attached to the liposome via a linker molecule associated with both the liposome and an oligonucleotide, trapped in the liposome, complexed with the liposome, dispersed in a lipid-containing solution, mixed with the lipid, combined with the lipid, contained in the lipid as a suspension, contained in micelles or complexed with micelles, or associated with the lipid in other way. The lipid, lipid/DNA or lipid/expression vector associated with a composition is not limited to any specific structure in the solution. For example, they may exist in a bimolecular structure as micelles or have a "collapsed" structure. They can also be simply dispersed in the solution, which may form aggregates of uneven size or shape. Lipids are fatty substances, which can be naturally occurring or synthetic lipids. For example, the lipids include fat droplets, which occur naturally in cytoplasms and in such compounds containing long-chain aliphatic hydrocarbons and their derivatives such as fatty acids, alcohols, amines, amino alcohols and aldehydes.

In a preferred embodiment of the present invention, the vector is a lentiviral vector.

Preparation

The present invention provides a preparation containing the heavy chain variable region according to the first aspect of the present invention, the heavy chain according to the second aspect of the present invention, the light chain variable region according to the third aspect of the present invention, the light chain according to the fourth aspect of the present invention, the antibody according to the fifth aspect of the present invention, the recombinant protein according to the sixth aspect of the present invention, the CAR construct according to the seventh aspect of the present invention, the immune cell according to the eighth aspect of the present invention, and/or the antibody-drug conjugate according to the ninth aspect of the present invention, and a pharmaceutically acceptable carrier, diluent or excipient. In one embodiment, the preparation is a liquid preparation. Preferably, the preparation is an injection. Preferably, the concentration of the CAR-T cells in the preparation is $1 \times 10^3$-$1 \times 10^9$ cells/ml, preferably $1 \times 10^5$-$1 \times 10^8$ cells/ml.

In one embodiment, the preparation may include a buffer such as neutral buffered saline, or sulfate buffered saline etc.; a carbohydrate such as glucose, mannose, sucrose or dextran, or mannitol; a protein; a polypeptide or amino acid such as glycine; an antioxidant; a chelating agent such as EDTA or glutathione; an adjuvant (for example, aluminum hydroxide); and a preservative. The preparation of the present invention is preferably administered for intravenous or intraperitoneal administration.

Therapeutic Application

The present invention includes a therapeutic application of cells (e.g., T cells) transduced with lentiviral vectors (LV) encoding expression cassettes of the present invention. The transduced T cells can target marker B7-H3 protein of tumor cells, and coordinately activate the T cells to cause cellular immune responses, thereby significantly improving their killing efficiency on the tumor cells from malignant tumors.

Therefore, the present invention also provides a method for stimulating a T cell-mediated immune response to a target cell population or tissue of a mammal, which includes the following step: administering the CAR-T cells of the present invention to the mammal.

In one embodiment, the present invention includes a type of cell therapy in which patient's autologous T cells (or heterologous donors) are isolated, activated and genetically modified to produce CAR-T cells, which are then injected into the same patient. In this way, the probability of suffering from graft-versus-host diseases is extremely low, and the antigens are recognized by T cells in a non-MHC-restricted manner. In addition, one kind of CAR-T can treat all cancers that express the antigen. Unlike antibody therapy, the CAR-T cells can replicate in vivo to achieve long-term persistence that can lead to sustained tumor control.

In one embodiment, the CAR-T cells of the present invention can undergo stable T cell expansion in vivo and last for an extended time. In addition, the CAR-mediated immune response can be part of an adoptive immunotherapy step in which CAR-modified T cells induce an immune response specific to the antigen binding domain in the CAR. For example, B7-H3 CAR-T cells cause a specific immune response against B7-H3 expressing cells.

Although the data disclosed herein specifically discloses a lentiviral vector including anti-B7-H3 scFv, hinge and transmembrane regions, and CD28 and/or 4-1BB (CD137), and a CD3ζ signal transduction domain, as well as an optional coding sequence of a self-cleaving protein and an optional coding sequence of a PD1-CD28 or PD1-IL7R fusion protein, but the present invention should be construed as including any number of changes to each of the construct components.

Cancers that can be treated include tumors that have not been vascularized or have not been substantially vascularized, as well as vascularized tumors. The cancers may include non-solid tumors (for example, hematological tumors such as leukemia and lymphomas) or solid tumors. The cancers treated with the CAR of the present invention include, but are not limited to, cancers, blastomas and sarcomas, and some leukemia or lymphoid malignancies, benign and malignant tumors, and malignant tumors, such as sarcomas, cancers, and melanomas. The cancers also includes adult tumors/cancers and childhood tumors/cancers.

The hematological cancers are cancers of the blood or bone marrow. Examples of the hematological (or hematogenic) cancers include leukemia, including acute leukemia (such as acute lymphoblastic leukemia, acute myelocytic leukemia, acute myeloid leukemia and myeloblastic, promyelocytic, myelomonocytic, monocytic and erythroleukemia), chronic leukemia (such as chronic myelocytic (granulocyte) leukemia, chronic myeloid leukemia, and chronic lymphocytic leukemia), polycythemia vera, lymphoma, Hodgkin's disease, non-Hodgkin's lymphoma (painless and high-grade forms), multiple myeloma, Waldenstrom's macroglobulinemia, heavy chain diseases, myelodysplastic syndromes, hairy cell leukemia, and myelodysplasia.

The solid tumors are abnormal lumps that usually do not contain cysts or tissues of fluid regions. The solid tumors may be benign or malignant. Different types of solid tumors are named by cell types that form them (such as sarcomas, cancers, and lymphomas). Examples of the solid tumors such as sarcomas and cancers include: head and neck tumors, throat cancer, lung cancer, non-small cell lung cancer, bronchial cancer, gastric cancer, peritoneal metastasis tumor of gastric cancer, esophageal cancer, liver cancer, bile duct cancer, pancreatic cancer, colorectal cancer, peritoneal metastatic tumor of colorectal cancer, small intestinal cancer, kidney tumor, kidney cancer, bladder tumor, transitional epithelial malignancies, endocrine tumors, thyroid cancer, adrenal tumors, breast cancer, cervical cancer, ovarian cancer, peritoneal metastatic tumor of ovarian cancer, endometrial cancer, choriocarcinoma, prostate cancer, testicular tumor, germ cell tumor, seminoma, embryogenic tumor, nervous system tumor, brain glioma, neuroblastoma, skin tumor, malignant melanoma, lymphoma, thymic tumor, nasopharyngeal cancer, bone cancer, sarcoma, rhabdomyosarcoma, liposarcoma, angiosarcoma, leiomyosarcoma, fibrosarcoma, osteosarcoma, Ewing's sarcoma, and solid metastatic tumors at the abdominal cavity, thoracic cavity, pelvic cavity and parenchymatous organs.

The CAR-T cells of the present invention can also be used as a type of vaccines for ex vivo immunization and/or in vivo therapy of mammals. Preferably, the mammals are humans.

For ex vivo immunization, at least one of the following occurs in vitro before the cells are administered into the mammals: i) expanding the cells, ii) introducing the CAR-encoding nucleic acid into the cells, and/or iii) cryopreserving the cells.

ex vivo procedures are well known in the art and will be discussed more fully below. Briefly, cells are isolated from mammals (preferably humans) and genetically modified (i.e., transduced or transfected in vitro) with vectors expressing the CAR disclosed herein. The CAR-modified cells can be administered to mammalian recipients to provide therapeutic benefits. The mammalian recipients may be humans, and the CAR-modified cells may be autologous relative to the recipients. Alternatively, the cells may be allogeneic, syngeneic, or xenogeneic relative to the recipients.

In addition to the use of cell-based vaccines for ex vivo immunization, the present invention also provides a composition and method for in vivo immunization to cause an immune response against an antigen in a patient.

The present invention provides a method for treating tumors, which includes administering an effective dose of CAR-modified T cells of the present invention to a subject in need.

The CAR-modified T cells of the present invention can be administered alone or as a pharmaceutical composition administered with diluent and/or with other components or other cytokines or cell populations. Briefly, the pharmaceutical composition of the present invention may include a target cell population as described herein, and one or more pharmaceutically or physiologically acceptable carriers, diluents or excipients. Such a composition may include a buffer such as neutral buffered saline, or sulfate buffered saline; a carbohydrate such as glucose, mannose, sucrose or dextran, or mannitol; a protein; a polypeptide or amino acid such as glycine; an antioxidant; a chelating agent such as EDTA or glutathione; an adjuvant (for example, aluminum hydroxide); and a preservative. The composition of the present invention is preferably administered for intravenous or intraperitoneal administration.

The pharmaceutical composition of the present invention can be administered in a manner suitable for a disease to be treated (or prevented). The number and frequency of administration are determined by the factors such as patient's condition, and the type and severity of the patient's disease, although the appropriate dose can be determined by clinical trials.

When referring to "immunologically effective dose", "anti-tumor effective dose", "tumor-suppressive effective dose" or "therapeutic dose", the precise dose of the composition of the present invention to be administered can be determined by the physician, who considers individual differences of patients (subjects) in age, weight, tumor size, degree of infection or metastasis, and symptom. It may generally be pointed out that the pharmaceutical composition including the T cells described herein may be administered at a dose of $10^3$ to $10^8$ cells/kg body weight, preferably a dose of $10^5$ to $10^6$ cells/kg body weight (including all integer values in those ranges). The T cell composition may also be administered multiple times at these doses. The cells can be administered by using injection techniques well known in immunotherapy (see, for example, Rosenberg et al., New Eng. J. of Med. 319:1676, 1988). The optimal dose and therapeutic schedule for a specific patient can be easily determined by a person skilled in the medical field by monitoring patient's signs of disease and adjusting the treatment accordingly.

The object composition can be administered in any convenient manner, including by spraying, injection, swallowing, infusion, implantation or transplantation. The composition described herein can be administered subcutaneously, intracutaneously, intratumorally, intranodally, intraspinally, or intramuscularly by intravenous (i.v.) injection, or in the body cavity such as abdominal cavity, pelvic cavity, chest cavity, ventricle, spinal cavity, or articular cavity to the patient. In one embodiment, the T cell composition of the present invention is administered to the patient by intradermal or subcutaneous injection. In another embodiment, the T cell composition of the present invention is preferably administered by i.v. injection. The composition of T cells can be injected directly into tumors, lymph nodes or sites of infection.

In some embodiments of the present invention, cells activated and expanded using the methods described herein or other methods known in the art for expanding T cells to therapeutic levels are administered to the patient in combination with any number of relevant treatment forms (e.g., before, at the same time or after). The treatment forms include but are not limited to treatment with the following reagents: the reagents such as antiviral therapy, cidofovir and interleukin-2, cytarabine (also known as ARA-C) or natalizumab treatment for MS patients or efalizumab treatment for psoriasis patients or other treatments for PML patients. In a further embodiment, the T cells of the present invention can be used in combination with chemotherapy, radiation, immunosuppressive agents, such as cyclosporine, azathioprine, methotrexate, mycophenolate mofetil and FK506, antibodies or other immunotherapeutic agents. In a further embodiment, the cell composition of the present invention is administered to the patient in combination with bone marrow transplantation, chemotherapeutic agents such as fludarabine, external beam radiotherapy (XRT), or cyclophosphamide (e.g., before, at the same time or after). For example, in one embodiment, the subject can undergo standard treatment of high-dose chemotherapy, followed by peripheral blood stem cell transplantation. In some embodiments, after transplantation, the subject receives an infusion of the expanded immune cells of the present invention. In an additional embodiment, the expanded cells are administered before or after surgery.

The dose of the above treatment administered to the patient varies with the precise nature of the condition being treated and the recipient of the treatment. The dose ratio for human administration can be implemented according to the practice accepted in the art. Generally, $1 \times 10^3$ to $1 \times 10^9$ modified T cells of the present invention can be administered to the patient per treatment or per course of treatment by, for example, intravenous infusion.

Detection Uses and Kit

The antibodies of the present invention can be used in test applications, for example, to test samples, thereby providing diagnostic information.

In the present invention, the samples (specimens) used include cells, tissue samples and biopsy samples. The term "biopsy" used in the present invention shall include all kinds of biopsy known to a person skilled in the art. Therefore, the biopsy used in the present invention may include, for example, tissue samples prepared by endoscopic methods or organ puncture or needle biopsy.

The samples used in the present invention include immobilized or preserved cell or tissue samples.

The present invention also provides a kit containing the antibody (or fragment thereof) and scFv of the present invention. In a preferred example of the present invention, the kit further includes a vessel, an instruction for use, a buffer, etc. In a preferred example, the antibody of the present invention can be immobilized on a test plate.

Main advantages of the present invention include:

(1) The antibody of the present invention has the characteristics of high affinity and high specificity.

(2) The humanized antibody or scFv of the present invention still has high affinity and high specificity for B7-H3.

(3) The engineered immune cells of the present invention can target tumor antigens (such as B7-H3), thereby selectively killing tumor cells.

(4) The engineered immune cells of the present invention can target proliferating vascular endothelial cells in tumors, and inhibit or damage tumor cells by destroying tumor angiogenesis and blood supply, so as to target tumor cells and tumor blood vessels at the same time and kill the tumor cells doubly and more effectively.

(5) The engineered immune cells of the present invention can target the tumor microenvironment, including but not limited to components such as fibroblasts or immune cells, so as to target tumor cells and tumor microenvironment at the same time and kill the tumor cells doubly and more effectively.

(6) The engineered immune cells of the present invention can co-express CARs targeting B7-H3 and CARs or secreted proteins targeting PD-L1, thereby enhancing the killing effect on tumor cells.

(7) In the present invention, the CAR targeting B7-H3 and the fusion protein targeting PD-L1 have a synergistic effect, which can improve the activation, proliferation, cytokine secretion and migration of CAR-T cells, increase the killing function of CAR-T cells in vivo, promote the migration and homing of CAR-T cells to tumor tissues, increase the retention time of CAR-T cells in vivo, and strengthen the ability to form memory cells. Therefore, compared with a single CAR, they can enhance the therapeutic effect of CAR-T cells, especially improve the effect of treating solid tumors with CAR-T cells.

(8) The present invention uses the single-chain antibody variable region (scFV) derived from the B7-H3 monoclonal antibody for the first time to construct B7-H3 specific CAR-T cells (B7-H3-CAR-T), which verifies the functions of B7-H3-CAR-T cells in vitro and in animal models and their therapeutic effects on multiple tumors.

(9) The B7-H3 monoclonal antibody of the present invention can be further applied to bispecific antibodies, ADC antibodies, biological reagents, clinical diagnostic reagents, imaging reagents, etc.

(10) The B7-H3 CAR cells and their new CAR structure and technology can be used not only for T cells to form CAR-T, but also for genetic modification and improvement of other immune cells, such as NK cells.

(11) The novel CAR-T structure and technology of the present invention can be used in combination with other targeting molecules for development and application.

The following further illustrates the present invention in combination with specific embodiments. It should be understood that these embodiments are only used for explaining the present invention, rather than limiting the scope of the present invention. The experimental methods unmarked with specific conditions in the following embodiments were carried out according to conventional conditions, for example, the conditions described in Sambrook et al., Molecular Cloning: A Laboratory Manual (New York: Cold Spring Harbor Laboratory Press, 1989), or according to the conditions recommended by the manufacturers. Unless otherwise specified, the percentages and parts were weight percentages and weight parts.

Unless otherwise specified, the materials and reagents used in the embodiments of the present invention were all commercially available products.

Example 1 Preparation of Antibodies

Balb/c mice were immunized using a humanized B7-H3 protein (a fusion protein of 4Ig-B7-H3 and mice IgG Fc fragments, 4Ig-B7-H3-mFc, self-made) as an antigen, mice serum was collected, and its affinity and titer for the B7-H3 protein were verified; and positive results show that anti-B7-H3 antibodies have been produced in the mice serum. Then, spleen cells of the successfully immunized mice were fused with SP2/0 cells to obtain hybridoma cells. ELISA and flow cytometry were used to screen positive monoclonal hybridoma cells against human B7-H3. A supernatant of the hybridoma cells was collected and purified to obtain B7-H3 mAb for antibody function verification.

Example 2 Measurement of Antibody Sequences

Total RNA was extracted from the monoclonal hybridoma cells with the kit and purified. cDNA of the monoclonal antibodies was obtained by reverse transcription of the RNA and amplification of 5'-RACE-cDNA. Using the obtained cDNA as a template, cDNA of the light chain and heavy chain variable regions of the monoclonal antibodies was obtained by PCR amplification, and then the cDNA of the variable regions of light chain and heavy chain was connected to plasmid vectors by TA vector cloning technology.

The heavy chain and light chain plasmids were transformed on competent bacteria, and monoclonal colonies were screened on a cloning plate.

The monoclonal colonies were picked, purified plasmids were extracted, and cDNA sequences of the light chain and heavy chain variable regions were obtained by conventional DNA sequencing.

The sequencing results of the antibody variable regions were compared with a database such as kabat, and CDR regions were identified to select correct antibody sequences.

Single-chain antibody fragments (scFv) were obtained by linking the heavy chain and light chain variable region sequences with linker peptides, and cloned to phIgV and pmIgV plasmid vectors. The scFv-phIgV or scFv-pmIgV vectors were transfected into 293T cells to prepare single-chain antibodies, and the functions of the single-chain antibodies were verified.

Example 3 Affinity and Specificity of B7-H3 Monoclonal Antibodies and Single-Chain Antibody scFv Thereof (1) Test on Specificity of B7-H3 Single-Chain Antibody scFv.

The labeled B7-H3 single-chain antibodies (scFv, self-made) were incubated with CHO cells expressing different B7 family molecules (including humanized B7-H1, B7-H3, B7-H4, and murine B7-H3 molecules) (self-made) for staining, respectively. A positive staining control experiment was carried out using the corresponding B7 family molecule antibodies, the primary CHO cells were used as a negative control, and the mice IgG antibodies were used as an isotype antibody control (isotope). Tested by flow cytometry, as shown in FIG. 1, the results show that the B7-H3 single-chain antibody scFv specifically recognizes and binds to B7-H3 molecules, but cannot bind to other B7 family molecules.

(2) Test on Affinity of B7-H3 Monoclonal Antibodies or scFv Thereof.

Under the same conditions, CHO cells stably expressing B7-H3 were stained with labeled anti-human B7-H3 monoclonal antibodies or anti-human B7-H3 single-chain antibody protein scFv at different concentrations respectively and incubated at 4° C. for 30 minutes, and the abilities of the two to bind to human B7-H3 were tested by flow cytometry and compared. The results are shown in FIG. 2. The B7-H3 monoclonal antibodies and single-chain antibodies (scFv) thereof have the same or equivalent binding ability to the B7-H3 molecules, and the both can effectively and specifically bind to humanized B7-H3 molecules.

Example 4 Expression of B7-H3 in Various Types of Tumor Cells

Figure 3:
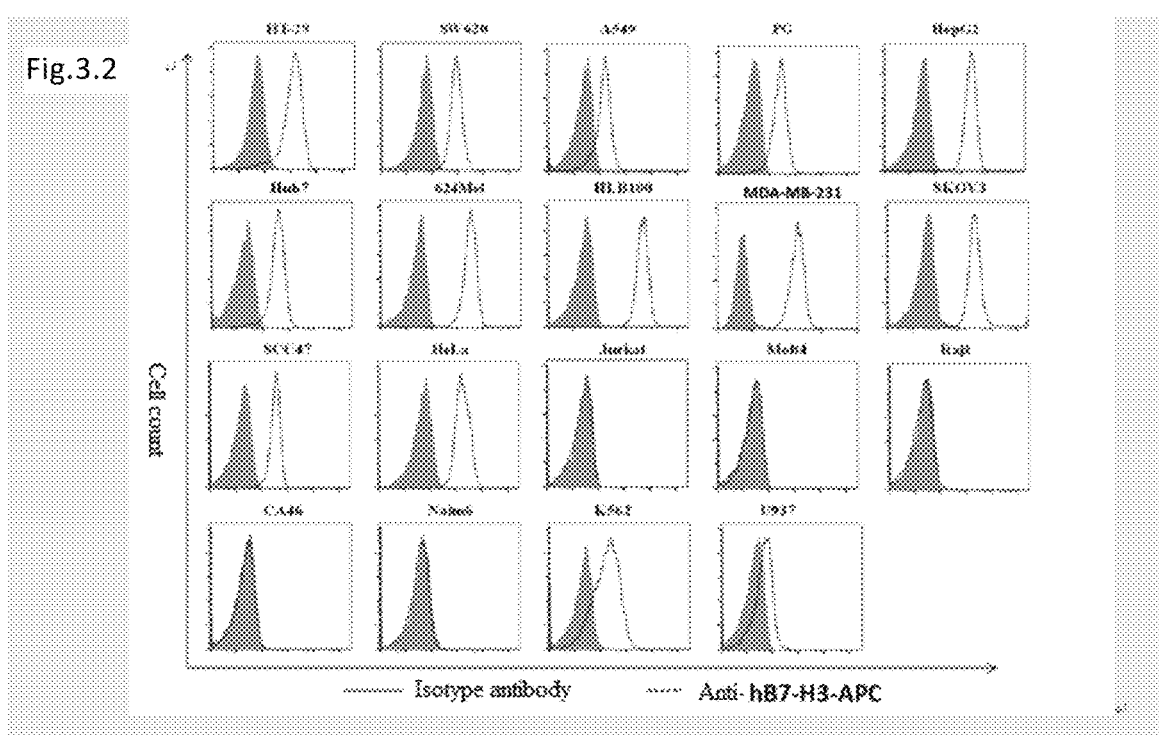
FIG. 3: expression of B7-H3 membrane protein on different types of tumor cells.

Immunohistochemical staining was performed on paraffin sections of multiple tumors: antigens were repaired by antigen retrieval method—citric acid/microwave steam bath at 100° C.; and immunohistochemical staining was performed using anti-B7-H3 mAb as primary antibodies and using an ABC complex kit and Streptavidin-HRP. The microscopic observations reveal that B7-H3 is highly expressed in multiple solid tumors, including colorectal cancer, ovarian cancer, breast cancer, gastric cancer, liver cancer, pancreatic cancer, prostate cancer, malignant glioma, neuroblastoma, head and neck tumors, malignant melanomas, etc., but not or lowly expressed in normal tissues. At the same time, B7-H3 may be expressed in vascular endothelial cells proliferating in solid tumors. part of the immunohistochemical results are shown in FIG. 3-1.

The anti-B7-H3 single-chain antibodies were used to measure the expression of B7-H3 on various tumor cell lines by flow cytometry, such as human colon cancer HT-29 cells, human colon cancer SW620 cells, human non-small lung cancer A549 cells, human pulmonary giant cell cancer PG cells, human liver cancer HepG2 cells, human liver cancer Huh7 cells, human melanoma 624Mel cells, HLB100, breast cancer MDA-MB-231 cells, ovarian cancer SKOV3 cells, squamous cell cancer SCC47 cells, cervical cancer HeLa cells, and human leukemia K562 cells. The results are shown in FIG. 3-2, which show that B7-H3 is highly expressed in multiple solid tumor cell lines and a small number of hematological tumor cell lines.

Example 5 B7-H3 CAR and Co-Expression Thereof with Different Molecules to Form New CAR-T Cells (1) Vector Construction By overlapping and extending the PCR technology, the anti-human B7-H3 single-chain antibody fragment (scFv), CD8 hinge region and transmembrane region, CD28 and/or 4-1BB intracellular signal transmission domain, and CD3ζ activation function domain were linked to construct a cDNA structure of CAR. By overlapping and extending the PCR technology, the extracellular fragment of PD-1 and the intracellular fragment of CD28, the extracellular fragment of PD-1 and the intracellular functional fragment (or intracellular mutant receptor fragment) of IL-7 receptor (IL-7R), were respectively linked to construct fusion cDNAs of PD1-CD28 (PD28) and PD1-IL-7R (PDCA7R). By overlapping and extending the PCR technology and using a T2A sequence as a cleaving linker sequence, the CAR cDNA was linked with PD28, or PDCA7R, and/or EGFP fragments respectively to construct gene structures of CAR molecules co-expressed with different molecules. The CAR with 4-1BB truncated and CD3 deleted was used as a control. The structures are shown in FIG. 4.

Figure 4:
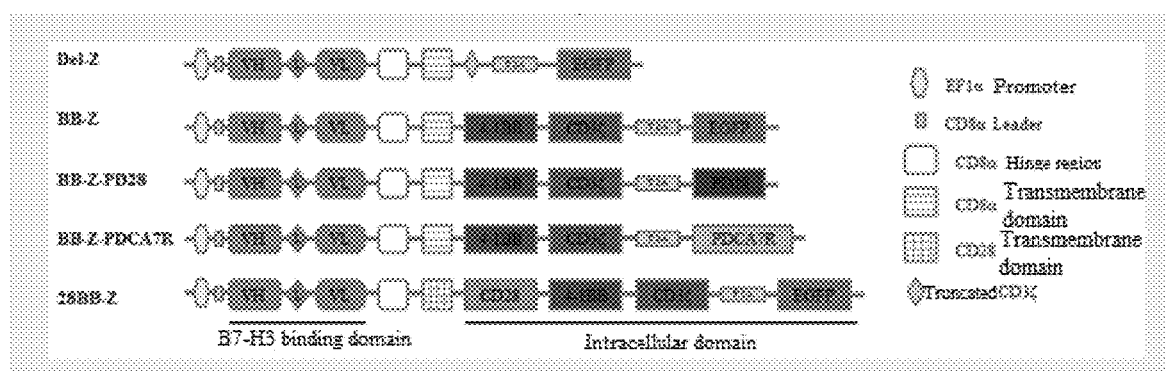
FIG. 4 is a schematic structural diagram of anti-B7-H3 chimeric antigen receptors or anti-B7-H3 chimeric antigen receptors of co-expressed molecules.

A typical CAR structure is shown in FIG. 4, where the amino acid sequence of the CAR structure containing co-expressed molecules is shown in SEQ ID NO.: 37, and the nucleotide sequence encoding the CAR structure containing co-expressed molecules is shown in SEQ ID NO.: 38.

(2) Preparation of B7-H3 CAR Lentiviral Vectors

The above-mentioned CARs of different structures or CAR structures containing co-expressed molecules were linked to lentiviral expression vectors by molecular cloning technology. Second- or third-generation lentiviral vectors were prepared and packaged on Lenti-X 293T cells or 293T cells by conventional PEI, calcium phosphate precipitation or other transfection methods. The lentiviral vector stock solution produced was filtered with a 0.45 μm filter and then concentrated by centrifugation; or purified by chromatography or ion exchange. The lentiviral vectors were quickly frozen in liquid nitrogen after titer identification, and then stored at −80° C.

(3) Preparation of B7-H3 CAR-T Cells

The lentiviral vectors and activated PBMCs or T cells were placed in a T cell culture medium containing IL-2 and then placed in an incubator, and the PBMCs or T cells were transfected with the viral vectors. After 48 hours of culture, the expression and phenotype of the CARs and the co-expressed molecules were tested. Later, the CAR-T cells of different structures were continuously cultured in the medium containing cytokines such as IL-2 (or IL-2, IL-7, IL-15) until harvested.

Example 6 Response of B7-H3 CAR-T Cells to Antigen Stimulation of Target Cells

The target cells irradiated with 100Gy were mixed with fresh B7-H3 CAR-T cells according to an effector-target ratio of 1:1 for stimulating 3 days, and CAR-T cells were counted after trypan blue staining. After that, the stimulation was repeated for 3 rounds of reaction, each round of reaction for 5-7 days, no exogenous cytokines were added during the process, and only half of the medium was changed. The total number of CAR-T cells was counted after each round of reaction.

The results are shown in FIG. 5. The data shows that the B7-H3 CAR-T cells of different structures can effectively proliferate after being stimulated by B7-H3 antigens; at the same time, the B7-H3 CAR-T cells co-expressing PDCA7R (BB-Z-PDCA7R CAR-T cells) have good proliferation ability.

Example 7 Immune Response of B7-H3 CAR-T Cells to Target Tumor Cells

After the B7-H3 CAR-T cells of different structures were incubated with target tumor cells irradiated with 100Gy or not irradiated, the CBA kit was used to test the secretion of various cytokines by flow cytometry. B7-H3-positive target tumor cells included B7-H3-positive hematological and solid malignancies, such as (but not limited to) breast cancer HLB100 cells, pulmonary giant cell carcinoma PG cells, ovarian cancer SKOV3 cells, and breast cancer MDA-MB-231 cells. The tumor cells with B7-H3 gene knocked out (such as MDA-MB-231-H3KO) were used as a negative target cell control.

The results are shown in FIG. 6, indicating that the B7-H3 CAR-T cells can release a large amount of Th1 cytokines such as interferon (IFN-γ) and interleukin 2 (IL-2) after co-cultivation stimulation by the B7-H3-positive target tumor cells. The BB-Z-PDCA7R CAR-T cells have the ability to induce the production of maximum cytokines, suggesting that the B7-H3 CAR-T cells have specificity to B7-H3 antigens, and the BB-Z-PDCA7R CAR-T cells have a higher activation function.

Example 8 Killing of Tumor Cells by B7-H3 CAR-T Cells

The CAR-T cells of different structures were respectively incubated with FarRed-labeled target tumor cells (human giant lung cell cancer PG cells, ovarian cancer SKOV3 cells, or breast cancer MDA-MB-231 cells) for 12 h according to different effector-target ratios (1:1, 5:1, 10:1, 15:1), and then stained with a reagent/kit such as DAPI or Annexin V, and the killing function of the CAR-T cells on the target tumor cells was tested by flow cytometry.

The results are shown in FIG. 7, indicating: the B7-H3 CAR-T cells of various structures can effectively kill B7-H3-positive tumor cells, and their killing function is antigen-specific.

Example 9 Anti-Tumor Effects of B7-H3 CAR-T Cells in Animal Models

NCG mice were subcutaneously injected with B7-H3-positive tumor cells (pulmonary giant cell cancer PG cells, or ovarian cancer SKOV3 cells) to establish tumor models. When the tumor diameter reached approximately 3-4 mm, mice in the SKOV3 group were intravenously injected with $5\times10^6$ CAR-T cells of different structures on the 12th, 20th, and 29th days; the mice in the PG group were intravenously injected with $5\times10^6$ CAR-T cells of different structures on the 5th, 10th and 15th days, respectively. and then tumor growth and survival time of the mice were tested.

The results are shown in FIG. 8, indicating that the B7-H3 CAR-T cells can effectively inhibit the growth of subcutaneous tumors. At the same time, the CAR-T cells with co-expressed molecules, including BB-Z-PD28 CAR-T and BB-Z-PDCA7R CAR-T cells, have better therapeutic effects.

Example 10 Combination Therapy of B7-H3 CAR-T Cells and PD-1 Antibodies to Improve Anti-Tumor Effect NCG mice were subcutaneously injected with $0.5\times10^6$ pulmonary giant cell cancer PG cells to establish subcutaneous tumor models. All the mice were randomly grouped (5 in each group). After 4-5 days, when the tumors reached an average diameter of about 4 mm, B7-H3 CAR-T cells (relatively low dose) were injected intravenously on the 5th, 9th and 15th days, respectively. The injection of anti-PD-1 antibodies was increased on the 6th and 11th days in the combination therapy group. The tumor sizes were measured with calipers twice a week.

The results are shown in FIG. 9. According to the data, the anti-PD-1 antibodies can significantly improve the anti-tumor effect of the B7-H3 CAR-T cells through combination therapy.

Example 11 Measurement of Humanized Antibody Activity and CAR-T Cell Killing Ability (1) Humanized Antibodies and Activity Measurement Thereof The variable region FR sequences of the obtained murine anti-B7-H3 antibodies were compared with human FR sequences and screened. After humanized mutation of the FR region sequences, humanized sequences of 3 light chains (L1, L2, L3) and 3 heavy chains (H1, H2, H3) were obtained respectively, and then, the affinity constants of 9 single-chain antibodies formed by the combinations of light chains and heavy chains were tested by Biacore. The results are shown in Table 1.

TABLE 1

| Name of single-chain antibody | Ka (1/Ms) | KD (1/s) | Full R^2 | KD (M) |
|---|---|---|---|---|
| Wild type (parental) | 8.89E+04 | 8.72E−06 | 0.9994 | 9.81E−11 |
| B7H3 CAR-H1L1 | 6.13E+04 | 2.30E−04 | 0.9939 | 3.76E−09 |

TABLE 1-continued

| Name of single-chain antibody | Ka (1/Ms) | KD (1/s) | Full R^2 | KD (M) |
|---|---|---|---|---|
| B7H3 CAR-H1L2 | 4.12E+04 | 6.44E−05 | 0.9966 | 1.56E−09 |
| B7H3 CAR-H1L3 | 4.11E+04 | 1.78E−04 | 0.9901 | 4.34E−09 |
| B7H3 CAR-H2L1 | 5.29E+04 | 3.06E−05 | 0.9925 | 5.78E−10 |
| B7H3 CAR-H2L2 | 5.48E+04 | 2.34E−05 | 0.9904 | 4.28E−10 |
| B7H3 CAR-H2L3 | 6.73E+04 | 8.74E−06 | 0.9859 | 1.30E−10 |
| B7H3 CAR-H3L1 | 7.16E+04 | 3.33E−05 | 0.9915 | 4.66E−10 |
| B7H3 CAR-H3L2 | 6.24E+04 | 3.26E−05 | 0.9948 | 5.23E−10 |
| B7H3 CAR-H3L3 | 4.25E+04 | 1.96E−05 | 0.9959 | 4.62E−10 |

(2) Measurement of the Killing Ability of Humanized B7-H3 CAR-T Cells

CAR-T cells were constructed from the humanized single-chain antibodies consisting of different light chain and heavy chain variable regions, The CAR-T cells of each combination were incubated with B7-H3-positive colon cancer LOVO cells for 8 hours, and their killing effect and cytokine secretion were tested. PBMCs and CD19 CAR-T cells were used as negative controls; B7-H3-negative LOVO cells (LOVO-KO, self-made) with B7-H3 gene knocked out were used as controls for target-negative tumor cells to verify tumor targeting specificity, and the results are shown in FIG. 10. It shows that the CAR-T cells derived from different combinations of single-chain antibodies have different killing effects on target cells, and different levels of secretion of cytokines IL-2 and IFN-γ.

From the above results, it can be seen that after humanization, different combinations of scFv have different affinities, and the affinities of different scFvs were related to the killing and immune response functions of the corresponding CAR-T cells. Therefore, selecting a single-chain antibody with appropriate affinity for the construction of CAR-T cells and herapeutic applications thereof will help optimize the anti-tumor activity of CAR-T cells and reduce side effects.

Example 12 Anti-Tumor Effects of Humanized B7-H3 CAR-T Cells on Different Tumors (1) In Vitro Killing Function Test The humanized B7-H3 CAR-T cells were incubated with labeled target tumor cells (colon cancer LOVO cells, ovarian cancer SKOV3 cells, gastric cancer HGC27 cells, or liver cancer MHCC7721 cells) according to different effector-target ratios at 4° C. for 12 h, and then stained with a reagent/kit such as DAPI or Annexin V, and the killing functions of the CAR-T cells on various target tumor cells and the release of cytokines were tested by flow cytometry.

The results are shown in FIGS. 11-1, 12-1, 13, and 14. The results show that: the humanized B7-H3 CAR-T cells can effectively kill tumor cells expressing B7-H3, and produce IL-2 and IFN-γ; and their killing function has antigen specificity.

(2) Anti-Tumor Effects in Animal Models

Luciferase-labeled colon cancer LOVO cells were injected into abdominal cavities of NCG mice ($5 \times 10^4$ Lovo cells/mouse) to establish colon cancer peritoneal tumor models. 4 days of after implantation, humanized B7-H3 CAR-T cells were injected intraperitoneally as a treatment group; and under the same conditions, CD19 CAR-T cells for treatment were used as a control group. Each dose was $1.0 \times 10^6$ cells/mouse, and the treatment was 2 times in total. The fluorescein intensities of tumor cells were tested on the 1st day before treatment and on the 21st, 28th, and 35th days after treatment to test and evaluate the growths of tumors.

Same as above, ovarian cancer SKOV3 cells were injected into abdominal cavities of NCG mice to establish ovarian cancer tumor models, and humanized B7-H3 CAR-T cells were used for intraperitoneal injection treatment with the same dose and method; and the growths of tumors were tested on the 0, 7th and 14th days after treatment.

The results show that the B7-H3 CAR-T cell therapy can effectively inhibit the growths of colon cancer and ovarian cancer peritoneal tumors, and eliminate tumors (see FIGS. 11-2 and 12-2), and prolong the survival time of mice. In the CD19 CAR-T cell control group and the PBS group, the tumors grow significantly and the survival time is short.

Example 13 Epitope Specificity of Anti-B7-H3 Monoclonal Antibodies

Competitive bindings of single-chain antibodies of the anti-B7-H3 monoclonal antibodies in this patent and single-chain antibodies of the existing anti-B7-H3 monoclonal antibodies (for example: MGA271, 84D[1]; Microgenesis, USA) were tested using flow cytometry and using 293T cells expressing humanized B7-H3 as target cells.

As shown in FIG. 15, B7-H3$^+$ 293T target cells are incubated with single-chain antibodies (84D-mIgG) of 10 ng, 1 ug, and 10 ug anti-B7-H3 monoclonal antibodies (MGA271, 84D) at 4° C. for 30 minutes, 100 ng biotin-labeled single-chain antibodies (H2L2-biotin) of the anti-B7-H3 antibodies in this patent were added, the target cells were washed with PBS containing 1% calf serum, PE-labeled anti-streptomycin (anti-SA) secondary antibodies were added, and the target cells were incubated at 4° C. for 20 minutes, washed and analyzed with a flow cytometer (FIG. 15A). Similarly, the experiment of competition between the B7-H3 single-chain antibodies and 84D single-chain antibodies was performed. 293T cells were incubated with 4 ug anti-84D-mIgG antibodies at 4° C. for 30 minutes, PE-labeled anti-mIgG secondary antibodies were added, then 100 ng, 2 ug, and 8ug anti-B7-H3 single-chain antibodies (H2L2-biotin) were added respectively after washing, and the cells were incubated for 1 h, washed and tested by flow cytometry (FIG. 15B).

The results show that there is no competitive binding between the anti-B7-H3 single-chain antibodies H2L2 and the 84D single-chain antibodies, indicating that the two monoclonal antibodies are bound to different epitopes of the B7-H3 molecules respectively.

REFERENCES

[1]. Loo D, et al. Development of an Fc-enhanced anti-B7-H3 monoclonal antibody with potent antitumor activity. Clin Cancer Res 2012 Jul. 15; 18(14):3834-45

All documents mentioned in the present invention were cited as references in this application, as if each document was individually cited as a reference. In addition, it should be understood that after reading the above teaching content of the present invention, a person skilled in the art can make various changes or modifications to the present invention, and these equivalent forms also fall within the scope defined by the appended claims of the present application.

The invention claimed is:

1. An antibody that binds B7-H3 comprising:
   (1) a heavy chain variable region; and
   (2) a light chain variable region,
   wherein the heavy chain variable region comprises the following three complementary determining regions (CDRs):
   CDR1 as shown in SEQ ID NO: 2,
   CDR2 as shown in SEQ ID NO: 5, and
   CDR3 as shown in SEQ ID NO: 8;
   the light chain variable region comprises the following three complementary determining regions (CDRs):
   CDR 1' as shown in SEQ ID NO: 11,
   CDR2' as shown in SEQ ID NO: 14, and
   CDR3' as shown in SEQ ID NO: 17.

2. A recombinant protein comprising:
   (i) the antibody of claim 1; and
   (ii) an optional tag sequence assisting expression and/or purification.

3. A CAR construct, wherein an antigen binding region of the CAR construct is an scFv that specifically binds to B7-H3, and the scFv has a heavy chain variable region and a light chain variable region, wherein the heavy chain variable region comprises the following three complementary determining regions (CDRs):
   CDR1 as shown in SEQ ID NO: 2,
   CDR2 as shown in SEQ ID NO: 5, and
   CDR3 as shown in SEQ ID NO: 8;
   the light chain variable region comprises the following three complementary determining regions (CDRs):
   CDR1' as shown in SEQ ID NO: 11,
   CDR2' as shown in SEQ ID NO: 14, and
   CDR3' as shown in SEQ ID NO: 17.

4. An engineered immune cell, wherein the immune cell comprises:
   (a) a first expression cassette for expressing the exogenous CAR construct of claim 3; and
   (b) an optional second expression cassette for expressing a fusion protein containing PD1-CD28 or PD1-IL7R.

5. An antibody-drug conjugate, wherein the antibody-drug conjugate comprises:
   (a) the antibody of claim 1; and
   (b) a conjugating portion conjugated to the antibody, wherein the conjugating portion is selected from the group consisting of detectable markers, drugs, toxins, cytokines, radionuclides, enzymes, and combinations thereof.

6. A method for treating a cancer or tumor comprising administering an effective amount of the antibody of claim 1, a recombinant protein comprising the antibody, an immune cell expressing the CAR construct, an antibody drug conjugate comprising the antibody, or a combination thereof to a subject in need thereof, wherein the CAR construct comprises an scFv having a heavy chain variable region and a light chain variable region,
   wherein the heavy chain variable region comprises the following three complementary determining regions (CDRs):
   CDR1 as shown in SEQ ID NO: 2,
   CDR2 as shown in SEQ ID NO: 5, and
   CDR3 as shown in SEQ ID NO: 8; and
   wherein the light chain variable region comprises the following three complementary determining regions (CDRs):
   CDR1' as shown in SEQ ID NO: 11,
   CDR2' as shown in SEQ ID NO: 14, and
   CDR3' as shown in SEQ ID NO: 17.

7. A pharmaceutical composition, wherein the pharmaceutical composition comprises:

the antibody of claim 1 and a pharmaceutically acceptable carrier, diluent or excipient.

8. A polynucleotide, wherein the polynucleotide encodes a polypeptide selected from the group consisting of:
(1) the antibody of claim 1;
(2) a recombinant protein comprising the antibody; and
(3) a CAR construct comprising an scFv having a heavy chain variable region and a light chain variable region,
wherein the heavy chain variable region comprises the following three complementary determining regions (CDRs):
CDR1 as shown in SEQ ID NO: 2,
CDR2 as shown in SEQ ID NO: 5, and
CDR3 as shown in SEQ ID NO: 8; and
wherein the light chain variable region comprises the following three complementary determining regions (CDRs):
CDR1' as shown in SEQ ID NO: 11,
CDR2' as shown in SEQ ID NO: 14, and
CDR3' as shown in SEQ ID NO: 17.

9. A vector, wherein the vector comprises the polynucleotide of claim 8.

10. A genetically engineered host cell, wherein the host cell comprises the vector of claim 9.

11. A method for preparing an engineered immune cell, comprising the following steps:
(A) providing an immune cell to be modified; and
(B) introducing a first expression cassette and an optional second expression cassette into the immune cell to be modified, wherein the first expression cassette expresses the CAR construct of claim 3, and the second expression cassette expresses a fusion protein containing PD1-CD28 or PD1-IL7R, thereby obtaining the engineered immune cell.

12. A method for testing a B7-H3 protein in a sample in vitro, comprising the following steps:
(1) contacting the sample with the antibody of claim 1 in vitro; and
(2) testing whether an antigen-antibody complex is formed, wherein the formation of the complex indicates the presence of the B7-H3 protein in the sample.

13. A test plate, wherein the test plate comprises: a substrate and a test strip, the test strip containing the antibody of claim 1.

14. A kit for preparing an engineered immune cell, wherein the kit comprises:
(a) a first container, and a first nucleotide sequence in the first container, the first nucleotide sequence containing a first expression cassette for expressing the CAR construct of claim 3; and
optionally (b) a second container, and a second nucleotide sequence in the second container, the second nucleotide sequence containing a second expression cassette for expressing a fusion protein.

15. A diagnostic kit, comprising:
(1) a first container containing the antibody of claim 1; and
(2) a second container containing a secondary antibody against the antibody of claim 1.

* * * * *

SEQUENCE LISTING

```
<160> NUMBER OF SEQ ID NOS: 39

<210> SEQ ID NO 1
<211> LENGTH: 8
<212> TYPE: PRT
<213> ORGANISM: artificial sequence
<220> FEATURE:
<223> OTHER INFORMATION: CDR1

<400> SEQUENCE: 1

Gly Leu Ser Phe Thr Gly Tyr Tyr
1               5

<210> SEQ ID NO 2
<211> LENGTH: 8
<212> TYPE: PRT
<213> ORGANISM: artificial sequence
<220> FEATURE:
<223> OTHER INFORMATION: CDR1

<400> SEQUENCE: 2

Gly Tyr Thr Phe Arg Asn Tyr Gly
1               5

<210> SEQ ID NO 3
<211> LENGTH: 8
<212> TYPE: PRT
<213> ORGANISM: artificial sequence
<220> FEATURE:
<223> OTHER INFORMATION: CDR1

<400> SEQUENCE: 3

Gly Tyr Thr Phe Ser Ser Tyr Trp
1               5

<210> SEQ ID NO 4
<211> LENGTH: 8
<212> TYPE: PRT
<213> ORGANISM: artificial sequence
<220> FEATURE:
<223> OTHER INFORMATION: CDR2

<400> SEQUENCE: 4

Ile Asn Phe Tyr Thr Gly Ala Thr
1               5

<210> SEQ ID NO 5
<211> LENGTH: 8
<212> TYPE: PRT
<213> ORGANISM: artificial sequence
<220> FEATURE:
<223> OTHER INFORMATION: CDR2

<400> SEQUENCE: 5

Ile Asn Thr Tyr Thr Gly Glu Pro
1               5

<210> SEQ ID NO 6
<211> LENGTH: 8
<212> TYPE: PRT
<213> ORGANISM: artificial sequence
<220> FEATURE:
<223> OTHER INFORMATION: CDR2

<400> SEQUENCE: 6

Ile Asp Pro Thr Ser Gly Asn Thr
1               5
```

```
<210> SEQ ID NO 7
<211> LENGTH: 9
<212> TYPE: PRT
<213> ORGANISM: artificial sequence
<220> FEATURE:
<223> OTHER INFORMATION: CDR3

<400> SEQUENCE: 7

Ala Ile Leu Gly Phe Ala Leu Asp Tyr
1               5

<210> SEQ ID NO 8
<211> LENGTH: 11
<212> TYPE: PRT
<213> ORGANISM: artificial sequence
<220> FEATURE:
<223> OTHER INFORMATION: CDR3

<400> SEQUENCE: 8

Ala Arg Trp Leu Arg His His Ala Met Asp Tyr
1               5                   10

<210> SEQ ID NO 9
<211> LENGTH: 12
<212> TYPE: PRT
<213> ORGANISM: artificial sequence
<220> FEATURE:
<223> OTHER INFORMATION: CDR3

<400> SEQUENCE: 9

Ala Arg Ile Phe Met Val Pro Tyr Tyr Phe Ala Tyr
1               5                   10

<210> SEQ ID NO 10
<211> LENGTH: 11
<212> TYPE: PRT
<213> ORGANISM: artificial sequence
<220> FEATURE:
<223> OTHER INFORMATION: CDR1'

<400> SEQUENCE: 10

Gln Ser Leu Val His Ser Asn Gly Asn Thr Tyr
1               5                   10

<210> SEQ ID NO 11
<211> LENGTH: 11
<212> TYPE: PRT
<213> ORGANISM: artificial sequence
<220> FEATURE:
<223> OTHER INFORMATION: CDR1'

<400> SEQUENCE: 11

Lys Ser Leu Leu His Ser Asn Gly Ile Thr Tyr
1               5                   10

<210> SEQ ID NO 12
<211> LENGTH: 5
<212> TYPE: PRT
<213> ORGANISM: artificial sequence
<220> FEATURE:
<223> OTHER INFORMATION: CDR1'

<400> SEQUENCE: 12

Ser Ser Val Ser Tyr
1               5
```

```
<210> SEQ ID NO 13
<211> LENGTH: 3
<212> TYPE: PRT
<213> ORGANISM: artificial sequence
<220> FEATURE:
<223> OTHER INFORMATION: CDR2'

<400> SEQUENCE: 13

Lys Ile Ser
1

<210> SEQ ID NO 14
<211> LENGTH: 3
<212> TYPE: PRT
<213> ORGANISM: artificial sequence
<220> FEATURE:
<223> OTHER INFORMATION: CDR2'

<400> SEQUENCE: 14

Gln Met Ser
1

<210> SEQ ID NO 15
<211> LENGTH: 3
<212> TYPE: PRT
<213> ORGANISM: artificial sequence
<220> FEATURE:
<223> OTHER INFORMATION: CDR2'

<400> SEQUENCE: 15

Leu Thr Ser
1

<210> SEQ ID NO 16
<211> LENGTH: 9
<212> TYPE: PRT
<213> ORGANISM: artificial sequence
<220> FEATURE:
<223> OTHER INFORMATION: CDR3'

<400> SEQUENCE: 16

Ser Gln Gly Thr His Val Pro Leu Thr
1               5

<210> SEQ ID NO 17
<211> LENGTH: 9
<212> TYPE: PRT
<213> ORGANISM: artificial sequence
<220> FEATURE:
<223> OTHER INFORMATION: CDR3'

<400> SEQUENCE: 17

Ala Gln Asn Leu Glu Leu Pro Leu Thr
1               5

<210> SEQ ID NO 18
<211> LENGTH: 9
<212> TYPE: PRT
<213> ORGANISM: artificial sequence
<220> FEATURE:
<223> OTHER INFORMATION: CDR3'

<400> SEQUENCE: 18

Gln Gln Trp Ser Ser Asp Pro Leu Thr
1               5
```

```
<210> SEQ ID NO 19
<211> LENGTH: 119
<212> TYPE: PRT
<213> ORGANISM: artificial sequence
<220> FEATURE:
<223> OTHER INFORMATION: the heavy chain variable region

<400> SEQUENCE: 19

Val His Ser Ala Val Gln Leu Gln Gln Ser Gly Pro Glu Leu Val Lys
1               5                   10                  15

Thr Gly Ala Ser Val Lys Ile Ser Cys Lys Thr Ser Gly Leu Ser Phe
            20                  25                  30

Thr Gly Tyr Tyr Met His Trp Val Thr Gln Ser Pro Gly Arg Ser Leu
        35                  40                  45

Glu Trp Ile Ala Tyr Ile Asn Phe Tyr Thr Gly Ala Thr Thr Tyr Asn
    50                  55                  60

Gln Lys Phe Met Gly Lys Ala Thr Phe Thr Val Asp Pro Ser Ser Asn
65                  70                  75                  80

Thr Ala Tyr Met Gln Phe Asn Ser Leu Thr Ser Glu Asp Ser Ala Val
                85                  90                  95

Tyr Tyr Cys Ala Ile Leu Gly Phe Ala Leu Asp Tyr Trp Gly Gln Gly
            100                 105                 110

Thr Ser Val Thr Val Ser Ser
        115

<210> SEQ ID NO 20
<211> LENGTH: 118
<212> TYPE: PRT
<213> ORGANISM: artificial sequence
<220> FEATURE:
<223> OTHER INFORMATION: the heavy chain variable region

<400> SEQUENCE: 20

Gln Ile Gln Leu Val Gln Ser Gly Pro Glu Leu Lys Lys Pro Gly Glu
1               5                   10                  15

Thr Val Lys Ile Ser Cys Lys Val Ser Gly Tyr Thr Phe Arg Asn Tyr
            20                  25                  30

Gly Met Ser Trp Val Lys Gln Thr Pro Gly Lys Asp Leu Lys Trp Met
        35                  40                  45

Gly Trp Ile Asn Thr Tyr Thr Gly Glu Pro Thr Tyr Ala Asp Asp Phe
    50                  55                  60

Arg Gly Arg Phe Thr Phe Ser Leu Glu Thr Ser Ala Ser Thr Ala Tyr
65                  70                  75                  80

Leu Gln Ile Asn Asn Leu Lys Asn Glu Asp Thr Ala Lys Tyr Phe Cys
                85                  90                  95

Ala Arg Trp Leu Arg His His Ala Met Asp Tyr Trp Gly Gln Gly Thr
            100                 105                 110

Ser Val Thr Val Ser Ser
        115

<210> SEQ ID NO 21
<211> LENGTH: 119
<212> TYPE: PRT
<213> ORGANISM: artificial sequence
<220> FEATURE:
<223> OTHER INFORMATION: the heavy chain variable region

<400> SEQUENCE: 21

Gln Val Gln Leu Gln Gln Ser Gly Ala Glu Leu Ala Lys Pro Gly Ala
1               5                   10                  15
```

```
Ser Val Lys Leu Ser Cys Lys Ala Ser Gly Tyr Thr Phe Ser Ser Tyr
            20                  25                  30

Trp Met His Trp Val Lys Gln Arg Pro Gly Gln Gly Leu Glu Trp Ile
            35                  40                  45

Gly Tyr Ile Asp Pro Thr Ser Gly Asn Thr Asn Tyr Asn Gln Lys Phe
        50                  55                  60

Lys Asp Lys Ala Thr Leu Ser Ala Asp Lys Ser Ser Ser Thr Ala Tyr
65                  70                  75                  80

Met Gln Leu Asn Ser Leu Thr Tyr Glu Asp Ser Ala Val Tyr Tyr Cys
                85                  90                  95

Ala Arg Ile Phe Met Val Pro Tyr Phe Ala Tyr Trp Gly Gln Gly
            100                 105                 110

Thr Ala Leu Thr Ile Ser Ser
            115
```

<210> SEQ ID NO 22
<211> LENGTH: 118
<212> TYPE: PRT
<213> ORGANISM: artificial sequence
<220> FEATURE:
<223> OTHER INFORMATION: the heavy chain variable region

<400> SEQUENCE: 22

```
Gln Ile Gln Leu Val Gln Ser Gly Ser Glu Leu Lys Lys Pro Gly Ala
1               5                   10                  15

Ser Val Lys Val Ser Cys Lys Val Ser Gly Tyr Thr Phe Arg Asn Tyr
            20                  25                  30

Gly Met Asn Trp Val Arg Gln Ala Pro Gly Gln Gly Leu Glu Trp Met
            35                  40                  45

Gly Trp Ile Asn Thr Tyr Thr Gly Glu Pro Thr Tyr Ala Gln Gly Phe
        50                  55                  60

Arg Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Trp Leu Arg His His Ala Met Asp Tyr Trp Gly Gln Gly Thr
            100                 105                 110

Leu Val Thr Val Ser Ser
            115
```

<210> SEQ ID NO 23
<211> LENGTH: 118
<212> TYPE: PRT
<213> ORGANISM: artificial sequence
<220> FEATURE:
<223> OTHER INFORMATION: the heavy chain variable region

<400> SEQUENCE: 23

```
Gln Ile Gln Leu Val Gln Ser Gly Ser Glu Leu Lys Lys Pro Gly Ala
1               5                   10                  15

Ser Val Lys Val Ser Cys Lys Val Ser Gly Tyr Thr Phe Arg Asn Tyr
            20                  25                  30

Gly Met Ser Trp Val Arg Gln Ala Pro Gly Gln Gly Leu Glu Trp Met
            35                  40                  45

Gly Trp Ile Asn Thr Tyr Thr Gly Glu Pro Thr Tyr Ala Gln Asp Phe
        50                  55                  60

Arg Gly Arg Phe Val Phe Ser Leu Asp Thr Ser Val Ser Thr Ala Tyr
```

```
                65                  70                  75                  80
Leu Gln Ile Ser Ser Leu Lys Ala Glu Asp Thr Ala Val Tyr Tyr Cys
                        85                  90                  95

Ala Arg Trp Leu Arg His His Ala Met Asp Tyr Trp Gly Gln Gly Thr
                100                 105                 110

Leu Val Thr Val Ser Ser
        115

<210> SEQ ID NO 24
<211> LENGTH: 118
<212> TYPE: PRT
<213> ORGANISM: artificial sequence
<220> FEATURE:
<223> OTHER INFORMATION: the heavy chain variable region

<400> SEQUENCE: 24

Gln Ile Gln Leu Val Gln Ser Gly Ser Glu Leu Lys Lys Pro Gly Ala
1               5                   10                  15

Ser Val Lys Val Ser Cys Lys Val Ser Gly Tyr Thr Phe Arg Asn Tyr
                20                  25                  30

Gly Met Ser Trp Val Arg Gln Ala Pro Gly Gln Gly Leu Glu Trp Met
            35                  40                  45

Gly Trp Ile Asn Thr Tyr Thr Gly Glu Pro Thr Tyr Ala Gln Asp Phe
        50                  55                  60

Arg Gly Arg Phe Val Phe Ser Leu Asp Thr Ser Val Ser Thr Ala Tyr
65                  70                  75                  80

Leu Gln Ile Asn Ser Leu Lys Ala Glu Asp Thr Ala Val Tyr Tyr Cys
                85                  90                  95

Ala Arg Trp Leu Arg His His Ala Met Asp Tyr Trp Gly Gln Gly Thr
                100                 105                 110

Leu Val Thr Val Ser Ser
        115

<210> SEQ ID NO 25
<211> LENGTH: 113
<212> TYPE: PRT
<213> ORGANISM: artificial sequence
<220> FEATURE:
<223> OTHER INFORMATION: the light chain variable region

<400> SEQUENCE: 25

Asp Val Val Met Thr Gln Thr Pro Leu Ser Leu Pro Val Ser Leu Gly
1               5                   10                  15

Asp Gln Ala Ser Ile Ser Cys Arg Ser Asn Gln Ser Leu Val His Ser
                20                  25                  30

Asn Gly Asn Thr Tyr Leu His Trp Tyr Leu Gln Lys Pro Gly Gln Ser
            35                  40                  45

Pro Lys Leu Leu Ile Tyr Lys Ile Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Phe Cys Ser Gln Gly
                85                  90                  95

Thr His Val Pro Leu Thr Phe Gly Ala Gly Thr Lys Leu Glu Leu Lys
                100                 105                 110

Arg
```

<210> SEQ ID NO 26
<211> LENGTH: 113
<212> TYPE: PRT
<213> ORGANISM: artificial sequence
<220> FEATURE:
<223> OTHER INFORMATION: the light chain variable region

<400> SEQUENCE: 26

```
Asp Val Val Met Thr Gln Thr Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Arg Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Ala Gly Ser Lys Leu Glu Leu Lys
            100                 105                 110

Arg
```

<210> SEQ ID NO 27
<211> LENGTH: 107
<212> TYPE: PRT
<213> ORGANISM: artificial sequence
<220> FEATURE:
<223> OTHER INFORMATION: the light chain variable region

<400> SEQUENCE: 27

```
Gln Ile Val Leu Thr Gln Ser Pro Ala Leu Met Ser Ala Ser Pro Gly
1               5                   10                  15

Glu Lys Val Thr Met Thr Cys Ser Ala Asn Ser Ser Val Ser Tyr Met
            20                  25                  30

Tyr Trp Tyr Gln Gln Lys Pro Arg Ser Ser Pro Lys Pro Trp Ile Tyr
        35                  40                  45

Leu Thr Ser Asn Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asp Pro Leu Thr
                85                  90                  95

Phe Gly Ala Gly Thr Lys Leu Glu Leu Lys Arg
            100                 105
```

<210> SEQ ID NO 28
<211> LENGTH: 113
<212> TYPE: PRT
<213> ORGANISM: artificial sequence
<220> FEATURE:
<223> OTHER INFORMATION: the light chain variable region

<400> SEQUENCE: 28

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30
```

```
Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gln Gly Thr Lys Leu Glu Ile Lys
                100                 105                 110

Arg

<210> SEQ ID NO 29
<211> LENGTH: 113
<212> TYPE: PRT
<213> ORGANISM: artificial sequence
<220> FEATURE:
<223> OTHER INFORMATION: the light chain variable region

<400> SEQUENCE: 29

Asp Val Val Met Thr Gln Ser Pro Leu Ser Asn Pro Val Thr Leu Gly
1               5                   10                  15

Thr Ser Ala Ser Ile Ser Cys Arg Ser Lys Ser Leu Leu His Ser
            20                  25                  30

Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gln Gly Thr Lys Leu Glu Ile Lys
                100                 105                 110

Arg

<210> SEQ ID NO 30
<211> LENGTH: 113
<212> TYPE: PRT
<213> ORGANISM: artificial sequence
<220> FEATURE:
<223> OTHER INFORMATION: the light chain variable region

<400> SEQUENCE: 30

Asp Val Val Met Thr Gln Thr Pro Leu Ser Leu Pro Val Thr Leu Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
            35                  40                  45

Pro Gln Leu Leu Ile Tyr Gln Met Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Leu Thr Phe Gly Gln Gly Thr Lys Leu Glu Ile Lys
```

100                 105                 110

Arg

<210> SEQ ID NO 31
<211> LENGTH: 21
<212> TYPE: PRT
<213> ORGANISM: artificial sequence
<220> FEATURE:
<223> OTHER INFORMATION: the signal peptide sequence of L1

<400> SEQUENCE: 31

Met Ala Leu Pro Val Thr Ala Leu Leu Pro Leu Ala Leu Leu Leu
1               5                   10                  15

His Ala Ala Arg Pro
            20

<210> SEQ ID NO 32
<211> LENGTH: 135
<212> TYPE: PRT
<213> ORGANISM: artificial sequence
<220> FEATURE:
<223> OTHER INFORMATION: the extracellular fragment of PD-1

<400> SEQUENCE: 32

Pro Gly Trp Phe Leu Asp Ser Pro Asp Arg Pro Trp Asn Pro Thr
1               5                   10                  15

Phe Ser Pro Ala Leu Leu Val Val Thr Glu Gly Asp Asn Ala Thr Phe
                20                  25                  30

Thr Cys Ser Phe Ser Asn Thr Ser Glu Ser Phe Val Leu Asn Trp Tyr
            35                  40                  45

Arg Met Ser Pro Ser Asn Gln Thr Asp Lys Leu Ala Ala Phe Pro Glu
        50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

Gln Ile Lys Glu Ser Leu Arg Ala Glu Leu Arg Val Thr Glu Arg Arg
        115                 120                 125

Ala Glu Val Pro Thr Ala His
    130                 135

<210> SEQ ID NO 33
<211> LENGTH: 59
<212> TYPE: PRT
<213> ORGANISM: artificial sequence
<220> FEATURE:
<223> OTHER INFORMATION: TM1

<400> SEQUENCE: 33

Pro Asp His Tyr Phe Lys Gly Phe Trp Ser Glu Trp Ser Pro Ser Tyr
1               5                   10                  15

Tyr Phe Arg Thr Pro Glu Ile Asn Asn Ser Ser Gly Glu Met Asp Pro
                20                  25                  30

Ile Leu Leu Thr Cys Pro Thr Ile Ser Ile Leu Ser Phe Phe Ser Val
            35                  40                  45

Ala Leu Leu Val Ile Leu Ala Cys Val Leu Trp
        50                  55

<210> SEQ ID NO 34
<211> LENGTH: 195
<212> TYPE: PRT
<213> ORGANISM: artificial sequence
<220> FEATURE:
<223> OTHER INFORMATION: C1

<400> SEQUENCE: 34

Lys Lys Arg Ile Lys Pro Ile Val Trp Pro Ser Leu Pro Asp His Lys
1               5                   10                  15

Lys Thr Leu Glu His Leu Cys Lys Lys Pro Arg Lys Asn Leu Asn Val
            20                  25                  30

Ser Phe Asn Pro Glu Ser Phe Leu Asp Cys Gln Ile His Arg Val Asp
        35                  40                  45

Asp Ile Gln Ala Arg Asp Glu Val Glu Gly Phe Leu Gln Asp Thr Phe
    50                  55                  60

Pro Gln Gln Leu Glu Glu Ser Glu Lys Gln Arg Leu Gly Gly Asp Val
65                  70                  75                  80

Gln Ser Pro Asn Cys Pro Ser Glu Asp Val Val Ile Thr Pro Glu Ser
                85                  90                  95

Phe Gly Arg Asp Ser Ser Leu Thr Cys Leu Ala Gly Asn Val Ser Ala
            100                 105                 110

Cys Asp Ala Pro Ile Leu Ser Ser Ser Arg Ser Leu Asp Cys Arg Glu
        115                 120                 125

Ser Gly Lys Asn Gly Pro His Val Tyr Gln Asp Leu Leu Leu Ser Leu
    130                 135                 140

Gly Thr Thr Asn Ser Thr Leu Pro Pro Pro Phe Ser Leu Gln Ser Gly
145                 150                 155                 160

Ile Leu Thr Leu Asn Pro Val Ala Gln Gly Gln Pro Ile Leu Thr Ser
                165                 170                 175

Leu Gly Ser Asn Gln Glu Glu Ala Tyr Val Thr Met Ser Ser Phe Tyr
            180                 185                 190

Gln Asn Gln
        195

<210> SEQ ID NO 35
<211> LENGTH: 404
<212> TYPE: PRT
<213> ORGANISM: artificial sequence
<220> FEATURE:
<223> OTHER INFORMATION: P component

<400> SEQUENCE: 35

Pro Gly Trp Phe Leu Asp Ser Pro Asp Arg Pro Trp Asn Pro Pro Thr
1               5                   10                  15

Phe Ser Pro Ala Leu Leu Val Val Thr Glu Gly Asp Asn Ala Thr Phe
            20                  25                  30

Thr Cys Ser Phe Ser Asn Thr Ser Glu Ser Phe Val Leu Asn Trp Tyr
        35                  40                  45

Arg Met Ser Pro Ser Asn Gln Thr Asp Lys Leu Ala Ala Phe Pro Glu
    50                  55                  60

Asp Arg Ser Gln Pro Gly Gln Asp Cys Arg Phe Arg Val Thr Gln Leu
65                  70                  75                  80

Pro Asn Gly Arg Asp Phe His Met Ser Val Val Arg Ala Arg Arg Asn
                85                  90                  95

Asp Ser Gly Thr Tyr Leu Cys Gly Ala Ile Ser Leu Ala Pro Lys Ala
            100                 105                 110

```
Gln Ile Lys Glu Ser Leu Arg Ala Glu Leu Arg Val Thr Glu Arg Arg
        115                 120                 125

Ala Glu Val Pro Thr Ala His Gly Gly Gly Ser Gly Gly Gly Gly
    130                 135                 140

Ser Gly Gly Gly Ser Pro Asp His Tyr Phe Lys Gly Phe Trp Ser
145                 150                 155                 160

Glu Trp Ser Pro Ser Tyr Tyr Phe Arg Thr Pro Glu Ile Asn Asn Ser
                165                 170                 175

Ser Gly Glu Met Asp Pro Ile Leu Leu Thr Cys Pro Thr Ile Ser Ile
            180                 185                 190

Leu Ser Phe Phe Ser Val Ala Leu Leu Val Ile Leu Ala Cys Val Leu
        195                 200                 205

Trp Lys Lys Arg Ile Lys Pro Ile Val Trp Pro Ser Leu Pro Asp His
    210                 215                 220

Lys Lys Thr Leu Glu His Leu Cys Lys Lys Pro Arg Lys Asn Leu Asn
225                 230                 235                 240

Val Ser Phe Asn Pro Glu Ser Phe Leu Asp Cys Gln Ile His Arg Val
                245                 250                 255

Asp Asp Ile Gln Ala Arg Asp Glu Val Glu Gly Phe Leu Gln Asp Thr
            260                 265                 270

Phe Pro Gln Gln Leu Glu Glu Ser Glu Lys Gln Arg Leu Gly Gly Asp
        275                 280                 285

Val Gln Ser Pro Asn Cys Pro Ser Glu Asp Val Val Ile Thr Pro Glu
    290                 295                 300

Ser Phe Gly Arg Asp Ser Ser Leu Thr Cys Leu Ala Gly Asn Val Ser
305                 310                 315                 320

Ala Cys Asp Ala Pro Ile Leu Ser Ser Ser Arg Ser Leu Asp Cys Arg
                325                 330                 335

Glu Ser Gly Lys Asn Gly Pro His Val Tyr Gln Asp Leu Leu Leu Ser
            340                 345                 350

Leu Gly Thr Thr Asn Ser Thr Leu Pro Pro Pro Phe Ser Leu Gln Ser
        355                 360                 365

Gly Ile Leu Thr Leu Asn Pro Val Ala Gln Gly Gln Pro Ile Leu Thr
    370                 375                 380

Ser Leu Gly Ser Asn Gln Glu Glu Ala Tyr Val Thr Met Ser Ser Phe
385                 390                 395                 400

Tyr Gln Asn Gln
```

<210> SEQ ID NO 36
<211> LENGTH: 1203
<212> TYPE: DNA
<213> ORGANISM: artificial sequence
<220> FEATURE:
<223> OTHER INFORMATION: the coding sequence of the P component

<400> SEQUENCE: 36

```
ccaggatggt tcttagactc cccagacagg ccctggaacc cccccacctt ctccccagcc      60
ctgctcgtgg tgaccgaagg ggacaacgcc accttcacct gcagcttctc caacacatcg     120
gagagcttcg tgctaaactg gtaccgcatg agccccagca accagacgga caagctggcc     180
gccttccccg aggaccgcag ccagcccggc caggactgcc gcttccgtgt cacacaactg     240
cccaacgggc gtgacttcca catgagcgtg gtcagggccc ggcgcaatga cagcggcacc     300
tacctctgtg gggccatctc cctggccccc aaggcgcaga tcaaagagag cctgcgggca     360
```

```
gagctcaggg tgacagagag aagggcagaa gtgcccacag cccacggtgg aggcggttca    420
ggcggaggtg gctctggcgg tggcggatcg cctgatcact attttaaagg cttctggagt    480
gaatggagtc caagttatta cttcagaact ccagagatca ataatagctc aggggagatg    540
gatcctatct tactaaccat cagcattttg agttttttct ctgtcgctct gttggtcatc    600
ttggcctgtg tgttatggaa aaaaggatt aagcctatcg tatggcccag tctccccgat     660
cataagaaga ctctggaaca tctttgtaag aaaccaagaa aaaatttaaa tgtgagtttc    720
aatcctgaaa gtttcctgga ctgccagatt catagggtgg atgacattca agctagagat    780
gaagtggaag gttttctgca agatacgttt cctcagcaac tagaagaatc tgagaagcag    840
aggcttggag gggatgtgca gagccccaac tgcccatctg aggatgtagt catcactcca    900
gaaagctttg aagagattc atccctcaca tgcctggctg ggaatgtcag tgcatgtgac    960
gcccctattc tctcctcttc caggtcccta gactgcaggg agagtggcaa gaatgggcct   1020
catgtgtacc aggacctcct gcttagcctt gggactacaa acagcacgct gccccctcca   1080
ttttctctcc aatctggaat cctgacattg aacccagttg ctcagggtca gcccattctt   1140
acttccctgg gatcaaatca agaagaagca tatgtcacca tgtccagctt ctaccaaaac   1200
cag                                                                 1203
```

<210> SEQ ID NO 37
<211> LENGTH: 934
<212> TYPE: PRT
<213> ORGANISM: artificial sequence
<220> FEATURE:
<223> OTHER INFORMATION: the amino acid sequence of CAR
<400> SEQUENCE: 37

```
Gln Ile Gln Leu Val Gln Ser Gly Ser Glu Leu Lys Lys Pro Gly Ala
1               5                   10                  15

Ser Val Lys Val Ser Cys Lys Val Ser Gly Tyr Thr Phe Arg Asn Tyr
            20                  25                  30

Gly Met Ser Trp Val Arg Gln Ala Pro Gly Gln Gly Leu Glu Trp Met
        35                  40                  45

Gly Trp Ile Asn Thr Tyr Thr Gly Glu Pro Thr Tyr Ala Gln Asp Phe
    50                  55                  60

Arg Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Trp Leu Arg His His Ala Met Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Asp Val Val Met Thr Gln Ser Pro Leu Ser Asn
    130                 135                 140

Pro Val Thr Leu Gly Thr Ser Ala Ser Ile Ser Cys Arg Ser Ser Lys
145                 150                 155                 160

Ser Leu Leu His Ser Asn Gly Ile Thr Tyr Leu Tyr Trp Tyr Leu Gln
                165                 170                 175

Lys Pro Gly Gln Ser Pro Gln Leu Leu Ile Tyr Gln Met Ser Asn Leu
            180                 185                 190

Ala Ser Gly Val Pro Asp Arg Phe Ser Gly Ser Gly Ser Gly Thr Asp
        195                 200                 205
```

-continued

Phe Thr Leu Lys Ile Ser Arg Val Glu Ala Glu Asp Val Gly Val Tyr
210                 215                 220

Tyr Cys Ala Gln Asn Leu Glu Leu Pro Leu Thr Phe Gly Gln Gly Thr
225                 230                 235                 240

Lys Leu Glu Ile Lys Thr Thr Thr Pro Ala Pro Arg Pro Pro Thr Pro
                245                 250                 255

Ala Pro Thr Ile Ala Ser Gln Pro Leu Ser Leu Arg Pro Glu Ala Cys
            260                 265                 270

Arg Pro Ala Ala Gly Gly Ala Val His Thr Arg Gly Leu Asp Phe Ala
            275                 280                 285

Cys Asp Ile Tyr Ile Trp Ala Pro Leu Ala Gly Thr Cys Gly Val Leu
290                 295                 300

Leu Leu Ser Leu Val Ile Thr Leu Tyr Cys Lys Arg Gly Arg Lys Lys
305                 310                 315                 320

Leu Leu Tyr Ile Phe Lys Gln Pro Phe Met Arg Pro Val Gln Thr Thr
                325                 330                 335

Gln Glu Glu Asp Gly Cys Ser Cys Arg Phe Pro Glu Glu Glu Glu Gly
            340                 345                 350

Gly Cys Glu Leu Arg Val Lys Phe Ser Arg Ser Ala Asp Ala Pro Ala
            355                 360                 365

Tyr Gln Gln Gly Gln Asn Gln Leu Tyr Asn Glu Leu Asn Leu Gly Arg
370                 375                 380

Arg Glu Glu Tyr Asp Val Leu Asp Lys Arg Gly Arg Asp Pro Glu
385                 390                 395                 400

Met Gly Gly Lys Pro Arg Arg Lys Asn Pro Gln Glu Gly Leu Tyr Asn
                405                 410                 415

Glu Leu Gln Lys Asp Lys Met Ala Glu Ala Tyr Ser Glu Ile Gly Met
            420                 425                 430

Lys Gly Glu Arg Arg Arg Gly Lys Gly His Asp Gly Leu Tyr Gln Gly
            435                 440                 445

Leu Ser Thr Ala Thr Lys Asp Thr Tyr Asp Ala Leu His Met Gln Ala
450                 455                 460

Leu Pro Pro Arg Arg Ala Lys Arg Gly Lys Pro Ile Pro Asn Pro Leu
465                 470                 475                 480

Leu Gly Leu Asp Ser Thr Ser Gly Ser Gly Ala Thr Asn Phe Ser Leu
                485                 490                 495

Leu Lys Gln Ala Gly Asp Val Glu Glu Asn Pro Gly Pro Met Ala Leu
            500                 505                 510

Pro Val Thr Ala Leu Leu Leu Pro Leu Ala Leu Leu Leu His Ala Ala
            515                 520                 525

Arg Pro Pro Gly Trp Phe Leu Asp Ser Pro Asp Arg Pro Trp Asn Pro
530                 535                 540

Pro Thr Phe Ser Pro Ala Leu Leu Val Val Thr Glu Gly Asp Asn Ala
545                 550                 555                 560

Thr Phe Thr Cys Ser Phe Ser Asn Thr Ser Glu Ser Phe Val Leu Asn
                565                 570                 575

Trp Tyr Arg Met Ser Pro Ser Asn Gln Thr Asp Lys Leu Ala Ala Phe
            580                 585                 590

Pro Glu Asp Arg Ser Gln Pro Gly Gln Asp Cys Arg Phe Arg Val Thr
            595                 600                 605

Gln Leu Pro Asn Gly Arg Asp Phe His Met Ser Val Val Arg Ala Arg
610                 615                 620

Arg Asn Asp Ser Gly Thr Tyr Leu Cys Gly Ala Ile Ser Leu Ala Pro

```
                625                 630                 635                 640
Lys Ala Gln Ile Lys Glu Ser Leu Arg Ala Glu Leu Arg Val Thr Glu
                    645                 650                 655
Arg Arg Ala Glu Val Pro Thr Ala His Gly Gly Gly Ser Gly Gly
                660                 665                 670
Gly Gly Ser Gly Gly Gly Gly Ser Pro Asp His Tyr Phe Lys Gly Phe
                    675                 680                 685
Trp Ser Glu Trp Ser Pro Ser Tyr Tyr Phe Arg Thr Pro Glu Ile Asn
                690                 695                 700
Asn Ser Ser Gly Glu Met Asp Pro Ile Leu Leu Thr Cys Pro Thr Ile
705                 710                 715                 720
Ser Ile Leu Ser Phe Phe Ser Val Ala Leu Leu Val Ile Leu Ala Cys
                    725                 730                 735
Val Leu Trp Lys Lys Arg Ile Lys Pro Ile Val Trp Pro Ser Leu Pro
                740                 745                 750
Asp His Lys Lys Thr Leu Glu His Leu Cys Lys Lys Pro Arg Lys Asn
                    755                 760                 765
Leu Asn Val Ser Phe Asn Pro Glu Ser Phe Leu Asp Cys Gln Ile His
                770                 775                 780
Arg Val Asp Asp Ile Gln Ala Arg Asp Glu Val Glu Gly Phe Leu Gln
785                 790                 795                 800
Asp Thr Phe Pro Gln Gln Leu Glu Glu Ser Glu Lys Gln Arg Leu Gly
                    805                 810                 815
Gly Asp Val Gln Ser Pro Asn Cys Pro Ser Glu Asp Val Val Ile Thr
                820                 825                 830
Pro Glu Ser Phe Gly Arg Asp Ser Ser Leu Thr Cys Leu Ala Gly Asn
                    835                 840                 845
Val Ser Ala Cys Asp Ala Pro Ile Leu Ser Ser Ser Arg Ser Leu Asp
                850                 855                 860
Cys Arg Glu Ser Gly Lys Asn Gly Pro His Val Tyr Gln Asp Leu Leu
865                 870                 875                 880
Leu Ser Leu Gly Thr Thr Asn Ser Thr Leu Pro Pro Pro Phe Ser Leu
                    885                 890                 895
Gln Ser Gly Ile Leu Thr Leu Asn Pro Val Ala Gln Gly Gln Pro Ile
                900                 905                 910
Leu Thr Ser Leu Gly Ser Asn Gln Glu Glu Ala Tyr Val Thr Met Ser
                    915                 920                 925
Ser Phe Tyr Gln Asn Gln
                    930

<210> SEQ ID NO 38
<211> LENGTH: 2793
<212> TYPE: DNA
<213> ORGANISM: artificial sequence
<220> FEATURE:
<223> OTHER INFORMATION: the coding sequence of CAR

<400> SEQUENCE: 38
gatgttgtga tgacgcagag tccactctcc aatccagtca ctcttggaac atcagcttcc    60
atctcctgca ggtctagtaa gagtctccta catagtaatg gcatcactta tttgtattgg   120
tatctgcaga agccaggcca gtctcctcag ctcctgattt atcagatgtc caaccttgcc   180
tcaggagtcc cagacaggtt cagtggcagt gggtcaggaa ctgatttcac actgaagatc   240
agcagagtgg aggctgagga tgtgggtgtt tattactgtg ctcaaaatct tgaacttccg   300
```

```
ctcacgttcg gtcagggac  caagctggag atcaaaggtg gaggcggttc aggcggaggt   360
ggctctggcg gtggcggatc gcagatccag ttggtgcagt ctggatctga actgaagaag   420
cctggagcgt cagtcaaggt ctcctgcaag gtttctgggt ataccttcag aaactatgga   480
atgagctggg tgaggcaggc tccaggacag ggtttagagt ggatgggctg ataaacacc    540
tacactggag agccaacata tgctcaagac ttcagggac  ggtttgtctt ctctttggat   600
acctctgtca gcactgccta tttgcagatc agtagcctca agctgagga  cacggctgtc   660
tattactgtg caagatggtt acgacaccat gctatggact actgggtca  aggaaccttg   720
gtcaccgtct cctcaaccac gacgccagcg ccgcgaccac caaccggc   gcccaccatc   780
gcgtcgcagc ccctgtccct gcgcccagag cgtcccggc  cagcggcggg gggcgcagtg   840
cacacgaggg ggctggactt cgcctgtgat atctacatct gggcgccctt ggccgggact   900
tgtgggtcc  ttctcctgtc actggttatc acccttact  gcaaacgggg cagaaagaaa   960
ctcctgtata tattcaaaca accatttatg agaccagtac aaaactactca agaggaagat  1020
ggctgtagct gccgatttcc agaagaagaa gaaggaggat gtgaactgcg ggtgaagttc  1080
agccggagcg ccgacgcccc tgcctaccag cagggccaga accagctgta caacgagctg  1140
aacctgggcc ggagggagga gtacgacgtg ctggacaagc ggagaggccg ggaccctgag  1200
atgggcggca agccccggag aaagaaccct caggagggcc tgtataacga actgcagaaa  1260
gacaagatgg ccgaggccta cagcgagatc ggcatgaagg cgagcggcg  gaggggcaag  1320
ggccacgacg gcctgtacca gggcctgagc accgccacca aggataccta cgacgccctg  1380
cacatgcagg ccctgccccc cagaagagcc aagcggggta agcctatccc taaccctctc  1440
ctcggtctcg attctacgag cggaagcgga gctactaact tcagcctgct gaagcaggct  1500
ggagacgtgg aggagaaccc tggacctatg gccctgcccg tgaccgccct gctgctgccc  1560
ctggccctgc tgctgcacgc cgccaggccg ccaggatggt tcttagactc cccagacagg  1620
ccctggaacc ccccaccctt ctccccagcc ctgctcgtgg tgaccgaagg ggacaacgcc  1680
accttcacct gcagcttctc caacacatcg agagcttcg  tgctaaactg gtaccgcatg  1740
agccccagca accagacgga caagctggcc gccttcccg  aggaccgcag ccagcccggc  1800
caggactgcc gcttccgtgt cacacaactg cccaacgggc gtgacttcca catgagcgtg  1860
gtcagggccc ggcgcaatga cagcggcacc tacctctgtg gggccatctc cctgccccc   1920
aaggcgcaga tcaaagagag cctgcgggca gagctcaggg tgacagagag aagggcagaa  1980
gtgcccacag cccacggtgg aggcggttca ggcggaggtg gctctggcgg tggcggatcg  2040
cctgatcact attttaaagg cttctggagt gaatggagtc aagttatta  cttcagaact  2100
ccagagatca ataatagctc agggagatg  gatcctatct tactaaccat cagcattttg  2160
agttttttct ctgtcgctct gttggtcatc ttggcctgtg tgttatggaa aaaaggatt   2220
aagcctatcg tatggcccag tctccccgat cataagaaga ctctggaaca tctttgtaag  2280
aaaccaagaa aaatttaaa  tgtgagtttc aatcctgaaa gttcctgga  ctgccagatt  2340
cataggggtgg atgacattca agctagagat gaagtggaag gtttctgca  agatacgttt  2400
cctcagcaac tagaagaatc tgagaagcag aggcttggag gggatgtgca gagccccaac  2460
tgcccatctg aggatgtagt catcactcca gaaagctttg aagagattc  atccctcaca  2520
tgcctggctg ggaatgtcag tgcatgtgac gcccctattc tctcctcttc aggtccccta  2580
gactgcaggg agagtggcaa gaatgggcct catgtgtacc aggacctcct gcttagcctt  2640
gggactacaa acagcacgct gccccctcca ttttctctcc aatctggaat cctgacattg  2700
```

```
aacccagttg ctcagggtca gcccattctt acttccctgg gatcaaatca agaagaagca    2760
tatgtcacca tgtccagctt ctaccaaaac cag                                2793

<210> SEQ ID NO 39
<211> LENGTH: 546
<212> TYPE: DNA
<213> ORGANISM: artificial sequence
<220> FEATURE:
<223> OTHER INFORMATION: the sequence of the promoter

<400> SEQUENCE: 39
aaggatctgc gatcgctccg gtgcccgtca gtgggcagag cgcacatcgc ccacagtccc      60
cgagaagttg gggggagggg tcggcaattg aacgggtgcc tagagaaggt ggcgcggggt     120
aaactgggaa agtgatgtcg tgtactggct ccgccttttt cccgagggtg ggggagaacc     180
gtatataagt gcagtagtcg ccgtgaacgt tctttttcgc aacgggtttg ccgccagaac     240
acagctgaag cttcgagggg ctcgcatctc tccttcacgc gcccgccgcc ctacctgagg     300
ccgccatcca cgccggttga gtcgcgttct gccgcctccc gcctgtggtg cctcctgaac     360
tgcgtccgcc gtctaggtaa gtttaaagct caggtcgaga ccgggccttt gtccggcgct     420
cccttggagc ctacctagac tcagccggct ctccacgctt tgcctgaccc tgcttgctca     480
actctacgtc tttgtttcgt tttctgttct gcgccgttac agatccaagc tgtgaccggc     540
gcctac                                                               546
```